(12) United States Patent
Katsuki et al.

(10) Patent No.: US 9,730,717 B2
(45) Date of Patent: Aug. 15, 2017

(54) MEDICAL MANIPULATOR SYSTEM

(75) Inventors: Ryohei Katsuki, Fujinomiya (JP);
Makoto Jinno, Fujinomiya (JP);
Shigeru Omori, Hadano (JP); Masao Hitotsuyanagi, Bad Homburg (DE);
Jack Marlotte, Ann Arbor, MI (US);
Deanna Hirzel, Chelsea, MI (US); Pari Shimoyama, Chicago, IL (US); Rie Nakamura, Ann Arbor, MI (US)

(73) Assignee: Karl Storz GmbH & Co. KG, Tuttlingen (DE)

( * ) Notice: Subject to any disclaimer, the term of this patent is extended or adjusted under 35 U.S.C. 154(b) by 676 days.

(21) Appl. No.: 13/020,407

(22) Filed: Feb. 3, 2011

(65) Prior Publication Data
US 2012/0203269 A1 Aug. 9, 2012

(51) Int. Cl.
*A61B 17/00* (2006.01)
*A61B 17/29* (2006.01)
(Continued)

(52) U.S. Cl.
CPC .............. *A61B 17/29* (2013.01); *A61B 34/70* (2016.02); *A61B 90/96* (2016.02); *A61B 90/98* (2016.02); *A61B 2017/00128* (2013.01); *A61B 2017/00132* (2013.01); *A61B 2017/00199* (2013.01); *A61B 2017/00398* (2013.01); *A61B 2017/00473* (2013.01); *A61B 2090/0803* (2016.02);
(Continued)

(58) Field of Classification Search
CPC ............ A61B 1/00059; A61B 1/00062; A61B 1/00055; A61B 19/44; A61B 19/22; A61B 2019/4815; A61B 2560/028; A61B 2560/0266; A61B 2018/00988; A61B 2019/4821; A61B 2019/4826; A61B 2019/4831
USPC ....... 606/205; 901/11; 700/79, 80, 175, 221, 700/225, 256
See application file for complete search history.

(56) References Cited

U.S. PATENT DOCUMENTS 4,996,975 A * 3/1991 Nakamura .................... 600/118
5,151,085 A * 9/1992 Sakurai et al. ................. 604/22
(Continued)

FOREIGN PATENT DOCUMENTS

JP 2008-104855 5/2008
JP 2009-106606 5/2009
(Continued)

OTHER PUBLICATIONS

U.S. Appl. No. 13/037,677, filed Mar. 1, 2011, Jinno, et al.
European Search Report Application No. EP 11 18 6423 completed: Jun. 30, 2016; Mailing Date: Jul. 12, 2016 9 pages.

*Primary Examiner* — Melanie Tyson
*Assistant Examiner* — Erin Colello
(74) *Attorney, Agent, or Firm* — Whitmyer IP Group LLC

(57) ABSTRACT

A medical manipulator system has an operating unit including a grip handle and a composite input unit, a working unit detachably mounted on the operating unit and including an end effector, and a controller for controlling the operating unit. The controller judges starting and ending of a surgical case and increments the usage count of the working unit based on a manner in which the working unit is mounted and dismounted, and the times at which the working unit is mounted and dismounted, and disables the working unit if the usage count of the working unit exceeds a preset count.

18 Claims, 14 Drawing Sheets

(51) Int. Cl.
*A61B 90/96* (2016.01)
*A61B 34/00* (2016.01)
*A61B 90/98* (2016.01)
*A61B 90/00* (2016.01)

(52) U.S. Cl.
CPC ............ *A61B 2090/0805* (2016.02); *A61B 2090/0814* (2016.02)

(56) References Cited

U.S. PATENT DOCUMENTS

| | | | |
|---|---|---|---|
| 5,359,993 A * | 11/1994 | Slater et al. .................. 600/133 |
| 5,383,874 A * | 1/1995 | Jackson et al. .................... 606/1 |
| 5,400,267 A * | 3/1995 | Denen .................... A61B 17/00 128/908 |
| 5,651,780 A * | 7/1997 | Jackson et al. .................... 606/1 |
| 5,830,121 A * | 11/1998 | Enomoto ........... A61B 1/00059 600/117 |
| 5,967,969 A * | 10/1999 | Enomoto et al. ............. 600/117 |
| 6,237,604 B1 * | 5/2001 | Burnside ............... A61B 90/90 128/897 |
| 6,298,255 B1 * | 10/2001 | Cordero ............ A61B 5/04085 600/372 |
| 6,308,089 B1 * | 10/2001 | von der Ruhr .......... A61B 5/00 600/338 |
| 6,331,181 B1 * | 12/2001 | Tierney et al. ............... 606/130 |
| 6,387,092 B1 * | 5/2002 | Burnside ............... A61B 18/14 606/32 |
| 6,436,032 B1 * | 8/2002 | Eto .................... A61B 1/00059 600/117 |
| 6,611,793 B1 * | 8/2003 | Burnside ............ A61B 18/1206 128/897 |
| 6,666,860 B1 * | 12/2003 | Takahashi ...... A61B 17/320068 606/34 |
| 6,761,698 B2 * | 7/2004 | Shibata et al. ..................... 601/2 |
| 6,793,652 B1 * | 9/2004 | Whitman et al. ................. 606/1 |
| 7,032,798 B2 * | 4/2006 | Whitman ........... A61B 10/0233 227/175.1 |
| 7,154,378 B1 * | 12/2006 | Ertas et al. .................. 340/5.85 |
| 7,479,140 B2 * | 1/2009 | Ellman .................. A61B 18/12 606/37 |
| 7,498,950 B1 * | 3/2009 | Ertas et al. ..................... 340/679 |
| 7,561,786 B1 * | 7/2009 | Black ............................ 396/57 |
| 7,835,823 B2 * | 11/2010 | Sillman et al. ............... 700/264 |
| 8,194,122 B2 * | 6/2012 | Amling et al. ................. 348/65 |
| 2002/0107538 A1 | 8/2002 | Shibata et al. ................ 606/169 |
| 2002/0188173 A1 * | 12/2002 | Kobayashi .......... A61B 1/00059 600/118 |
| 2003/0093103 A1 | 5/2003 | Malackowski et al. ...... 606/170 |
| 2003/0174205 A1 * | 9/2003 | Amling ............. A61B 1/00059 348/65 |
| 2003/0208196 A1 * | 11/2003 | Stone .............................. 606/41 |
| 2004/0133189 A1 * | 7/2004 | Sakurai ............................ 606/1 |
| 2005/0113815 A1 * | 5/2005 | Ritchie ................. A61B 18/20 606/15 |
| 2006/0149126 A1 * | 7/2006 | Ertas et al. .................... 600/101 |
| 2007/0083286 A1 * | 4/2007 | Kobayashi .................... 700/214 |
| 2007/0156285 A1 | 7/2007 | Sillman et al. |
| 2008/0249551 A1 * | 10/2008 | Sunaoshi ............... A61B 19/22 606/170 |
| 2008/0262654 A1 * | 10/2008 | Omori .................... A61B 90/96 700/245 |
| 2008/0300580 A1 * | 12/2008 | Shelton et al. .................... 606/1 |
| 2009/0036901 A1 * | 2/2009 | Omori .................... A61B 19/22 606/130 |
| 2009/0054889 A1 * | 2/2009 | Newton ................. A61B 18/12 606/33 |
| 2009/0062814 A1 * | 3/2009 | Omori .................... A61B 19/22 606/130 |
| 2009/0112229 A1 | 4/2009 | Omori et al. |
| 2009/0131756 A1 * | 5/2009 | Nemoto ........................ 600/300 |
| 2010/0204713 A1 * | 8/2010 | Ruiz Morales ............... 606/130 |

FOREIGN PATENT DOCUMENTS

| | | |
|---|---|---|
| WO | 9414129 A1 | 6/1994 |
| WO | 03013372 A2 | 2/2003 |
| WO | 2010126127 A1 | 11/2010 |

* cited by examiner

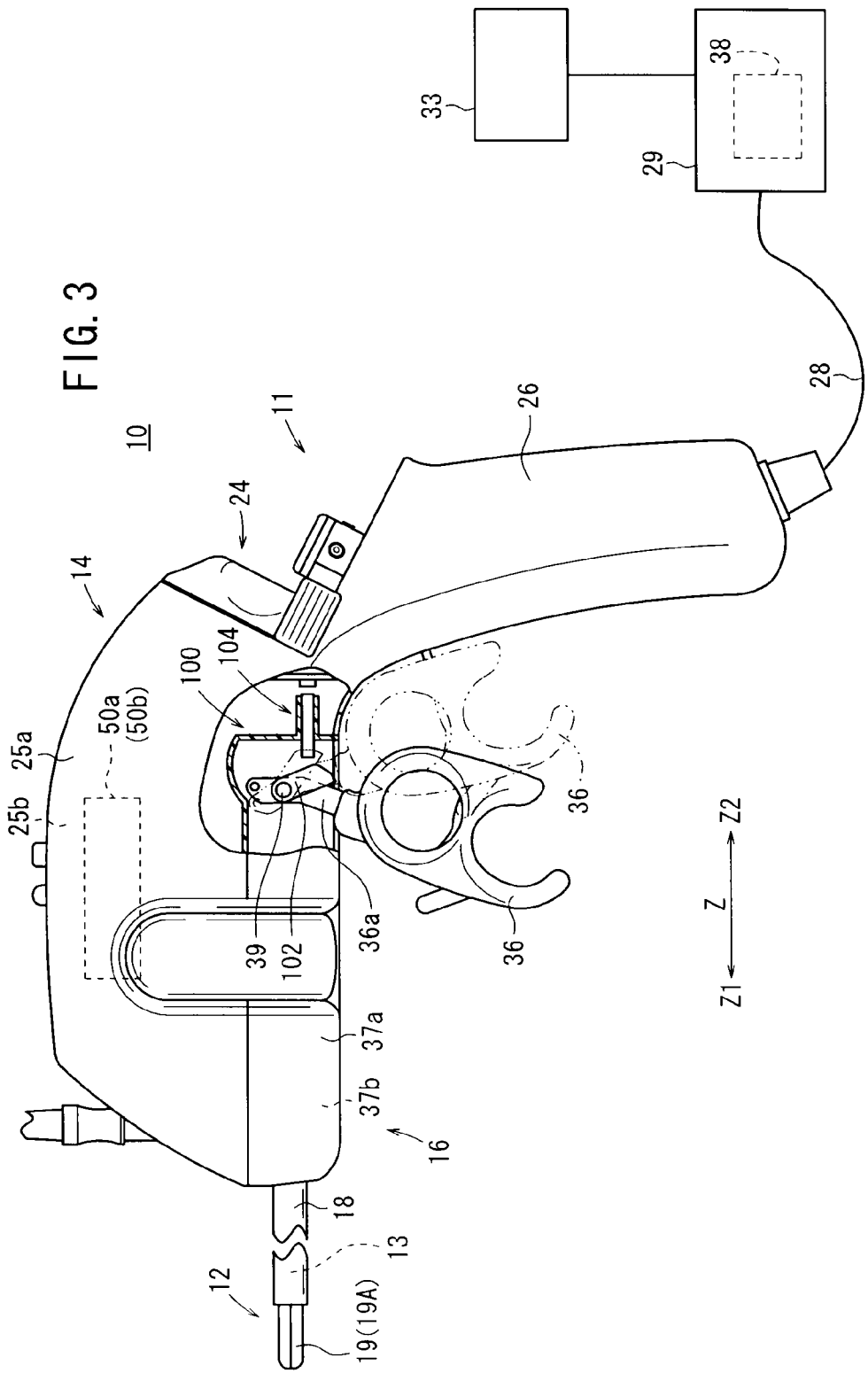

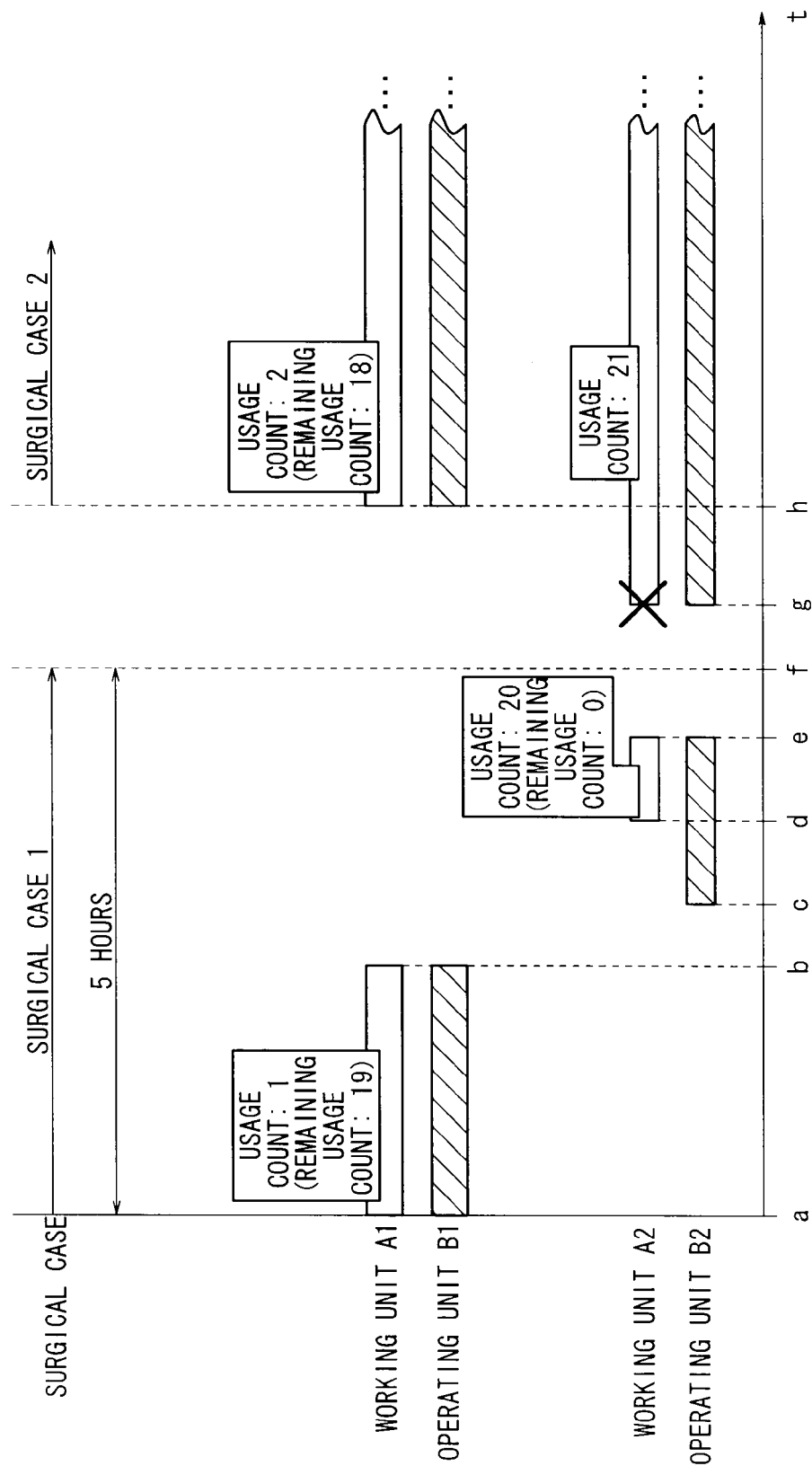

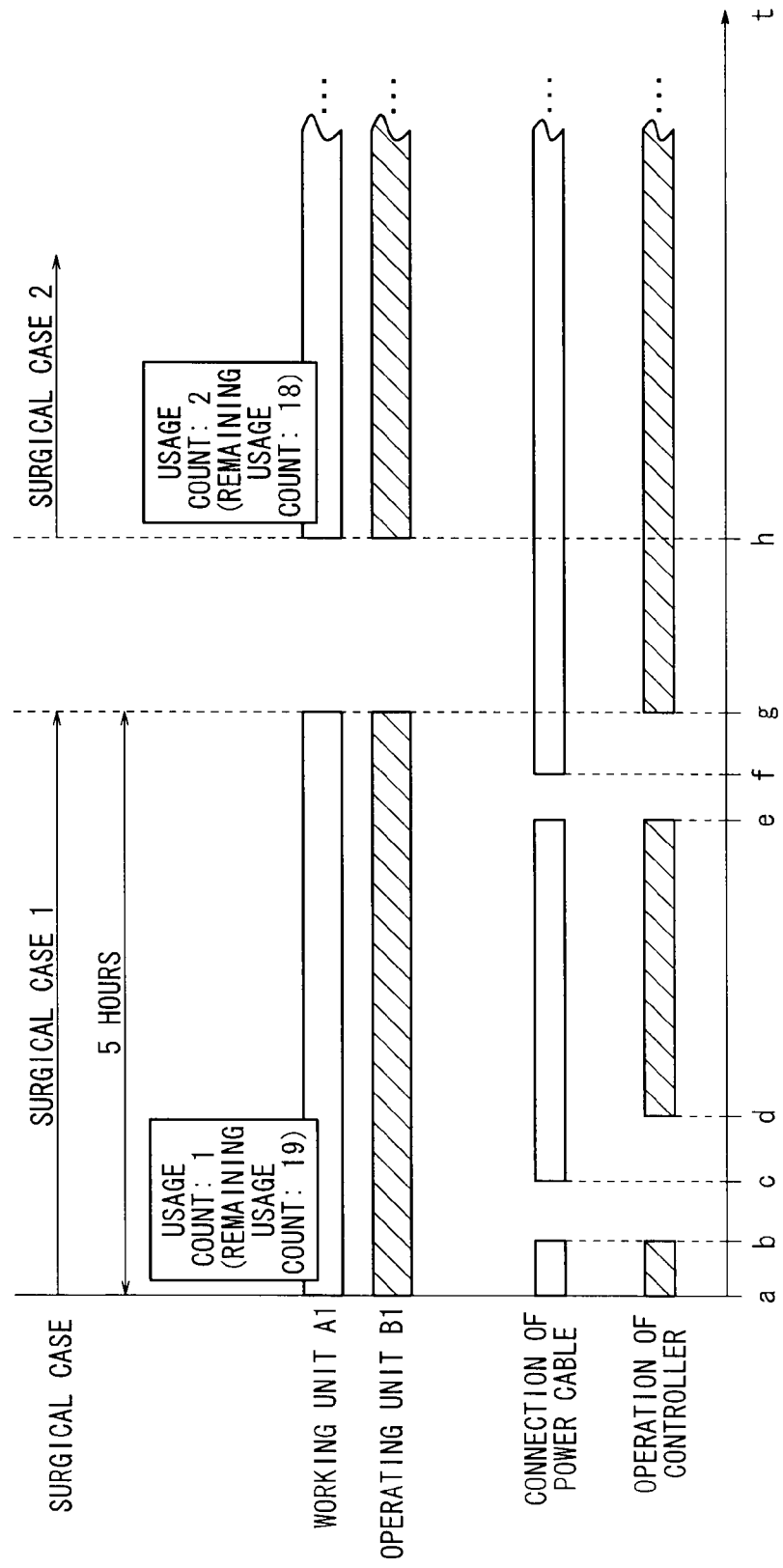

MEDICAL MANIPULATOR SYSTEM

BACKGROUND OF THE INVENTION

Field of the Invention

The present invention relates to a medical manipulator system having an operating unit with an input member operable to enter input actions, and a working unit having an end effector such as a gripper or the like mounted on the distal end of a shaft, the working unit being detachably mounted on the operating unit.

Description of the Related Art

According to endoscopic surgery (also called laparoscopic surgery), it is customary to form a plurality of holes or incisions in the abdominal region of a patient, insert trocars (tubular instruments) into the respective incisions, and introduce a laparoscope and a plurality of pairs of forceps through the trocars into the body cavity. End effectors such as a gripper for gripping a living tissue, scissors, a blade of an electrical scalpel, etc., are mounted on distal ends of the forceps. After the laparoscope and the forceps have been inserted into the body cavity, a surgeon actuates the forceps to perform a surgical operation while watching images of the inside of the body cavity, which are displayed on a display monitor electrically connected to the laparoscope. Since the laparoscopic surgical operation procedure does not require a laparotomy, the operation is less burdensome on the patient, and greatly reduces the number of days required for the patient to spend before recovering from the operation and being released from the hospital. Laparoscopic surgery is expected to increase the range of surgical operations to which it is applicable.

Japanese Laid-Open Patent Publication No. 2008-104855 discloses a medical manipulator including a forceps to be inserted through trocars, such as forceps the distal ends of which have a plurality of joints that change the attitude of the distal ends, in addition to general forceps the distal ends of which do not have joints. The disclosed medical manipulator is capable of producing motions with high degrees of freedom within body cavities, thus making it easy for a surgeon to perform various surgical techniques, and is applicable to a wide variety of surgical cases.

The medical manipulator disclosed in Japanese Laid-Open Patent Publication No. 2008-104855 comprises a working unit including a distal-end working unit having an end effector and joints, and an operating unit having an actuator for actuating the distal-end working unit. The working unit is detachably mounted on the operating unit. While the working unit is mounted on the operating unit, drive power from the actuator is transmitted to the distal-end working unit in order to operate the distal-end working unit.

The working unit includes wires, for example, as power transmitting members. However, wires tend to deteriorate, e.g., become elongated, while in use, possibly causing the distal-end working unit to fail to operate properly. One solution would be to establish a certain upper limit for the number of times that the working unit has been used (usage count), and to forcibly disable the working unit when the usage count of the working unit reaches a preset upper limit (limit usage count). In this regard, Japanese Laid-Open Patent Publication No. 2008-104855 discloses that a usage count of the working unit may be stored and managed by a usage history management table.

However, Japanese Laid-Open Patent Publication No. 2008-104855 discloses nothing concerning a means for forcibly limiting use of the working unit when the usage count thereof reaches the limit usage count.

SUMMARY OF THE INVENTION

It is an object of the present invention to provide a medical manipulator system, which is capable of forcibly limiting use of a working unit thereof when the usage count thereof reaches a preset limit usage count.

According to the present invention, there is provided a medical manipulator system comprising a manipulator including a working unit with an end effector mounted on a distal end thereof and an operating unit having an operation input unit operable to enter an operation command, and an actuator energizable depending on an operation command entered by the operation input unit for actuating the end effector, the working unit being detachably mounted on the operating unit, a controller for controlling the actuator and incrementing a usage count of the working unit, the operating unit being connectable to the controller, and a usage history holder for holding usage history data of the working unit, wherein the working unit includes an ID holder for holding individual identifying information of the working unit, the operating unit includes an ID detector for detecting the individual identifying information held by the ID holder, and the controller judges starting and ending of a surgical case based on a manner in which the working unit is mounted and dismounted and the times at which the working unit is mounted and dismounted, counts a single usage event of the working unit when the surgical case has started or ended, and disables the working unit if the usage count of the working unit exceeds a preset count.

The controller increments the usage count of the working unit based on the manner in which the working unit is mounted and dismounted and the times at which the working unit is mounted and dismounted. If the usage count of the working unit exceeds a preset count (limit usage count), then the controller disables the working unit. Therefore, even if the operator of the manipulator system operates the operation input unit, the actuator cannot be energized. In other words, since the operation command entered by the operation input unit is canceled, the working unit including the end effector is not actuated. A working unit, the usage count of which has reached the limit usage count, therefore is forcibly disabled.

In the above medical manipulator system, the controller may increment the usage count of the working unit each time a surgical case has started and when the working unit satisfies a usage starting condition, and may increment the usage count of the working unit each time a first preset time is exceeded if the working unit is used beyond the first preset time during a surgical case.

During one surgical case, the manipulator system increments the usage count of the working unit each time that the usage time thereof exceeds the first preset time. Consequently, the working unit is prevented from being used infinitely and hence from suffering from a durability problem.

In the medical manipulator system, if the usage count of the working unit exceeds the present count because the working unit has been used beyond the first preset time during the surgical case, the controller may allow the working unit to operate until a special preset time that is longer than the first preset time is reached.

Therefore, since the time for which the working unit can be used is extended only for a final usage event of the working unit, the working unit is prevented from becoming disabled while in use during the final usage event, and hence a surgical operation can be performed smoothly in the surgical case.

In the medical manipulator system, the controller may measure a parameter that increases as the working unit is used, and may increment the usage count of the working unit when the parameter reaches a reference value, which is determined depending on the usage count of the working unit during a surgical case even before the first preset time has elapsed.

Since the usage count of the working unit is incremented while reflecting an actual manner in which the working unit is used, the time at which the working unit is disabled based on the usage count thereof is optimized.

In the medical manipulator system, the controller may define a surgical case based on at least one rule. In this case, the controller determines whether the surgical case has been switched to another surgical case, sets a first preset time as a maximum time regarded as a surgical case, and increments the usage count of the working unit for each surgical case.

Since the controller regards usage of the working unit within the first preset time as a single usage event, the controller judges that the surgical case has not been switched to another surgical case each time that the usage time of the working unit exceeds the first preset time. If the surgical case takes a considerable length of time, then the controller regards usage of the working unit as a plurality of usage events, and increments the usage count of the working unit accordingly. Consequently, the time at which the working unit is disabled based on the usage count thereof is optimized.

In the medical manipulator system, if the operating unit is disconnected from the controller and thereafter is reconnected to the controller while the controller remains energized, then the controller may judge that the surgical case has not been switched to another surgical case when the operating unit is reconnected to the controller within a second preset time, which is shorter than the first preset time, after the operating unit has been disconnected from the controller, and may judge that the surgical case has been switched to another surgical case when the operating unit is reconnected to the controller beyond the second preset time after the operating unit has been disconnected from the controller.

The controller determines whether or not the surgical case has been switched to another surgical case based on whether the operating unit remains disconnected from the controller within the second preset time. For example, the shortest period that is expected to be required for disconnecting the operating unit from the controller and for sterilizing the operating unit is preset as the second preset time. Therefore, the controller can determine whether or not the surgical case has been switched to another surgical case, or whether the operating unit has been replaced due to an error, and can increment the usage count of the working unit appropriately.

In the medical manipulator system, if the controller is restarted after the controller has not been supplied with electric power, or has been turned off to result in a power-off state, the controller may judge that the surgical case has not been switched to another surgical case when restarting of the controller is completed within a third preset time, which is shorter than the first preset time, after start of the power-off state, and may judge that the surgical case has been switched to another surgical case when restarting of the controller is completed beyond the third preset time after start of the power-off state.

The controller determines whether the surgical case has been switched to another surgical case or not based on whether restarting of the controller is completed within the third preset time from start of the power-off state. If the power switch of the controller is inadvertently turned off, or if the power cable is inadvertently disconnected from the controller, then the controller can determine whether the surgical case has been switched to another surgical case or whether the controller has inadvertently been turned off, by setting the third preset time so as to correspond to a maximum time that is expected to be required to restart the controller. As a result, the controller can appropriately increment the usage count of the working unit.

In the medical manipulator system, the controller may have N connection ports for connection to operating units, and the controller may judge that the surgical case has been switched to another surgical case when the number of operating units connected to the controller during the surgical case reaches $N+\alpha$.

Accordingly, when an nth operating unit, where "n" is $\alpha$ greater than the number N of connection ports, is immediately connected to the controller while the controller remains energized, the controller is prevented from failing to recognize that the surgical case has actually been switched to a next surgical case. Therefore, the usage count of the working unit can be incremented appropriately.

In the medical manipulator system, $\alpha$ may be 2.

Even if an nth operating unit, where "n" is 1 greater than the number N of connection ports, is connected, the controller does not judge that the surgical case has been switched to another surgical case. Consequently, even when an operating unit has to be replaced due to error, the usage count of an operating unit, which has already been connected, is not unduly incremented. Thus, the usage count of the working unit can be incremented appropriately.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a side elevational view, partially omitted from illustration, of the manipulator, with the working unit being mounted on the operating unit;

FIG. 4B is an enlarged fragmentary cross-sectional view of the detecting mechanism with the trigger lever being pulled in;

FIG. 13 is a diagram illustrative of a second rule for defining a surgical case; and FIG. 14 is a diagram illustrative of a third rule for defining a surgical case.

DESCRIPTION OF THE PREFERRED EMBODIMENTS

Figure 1:
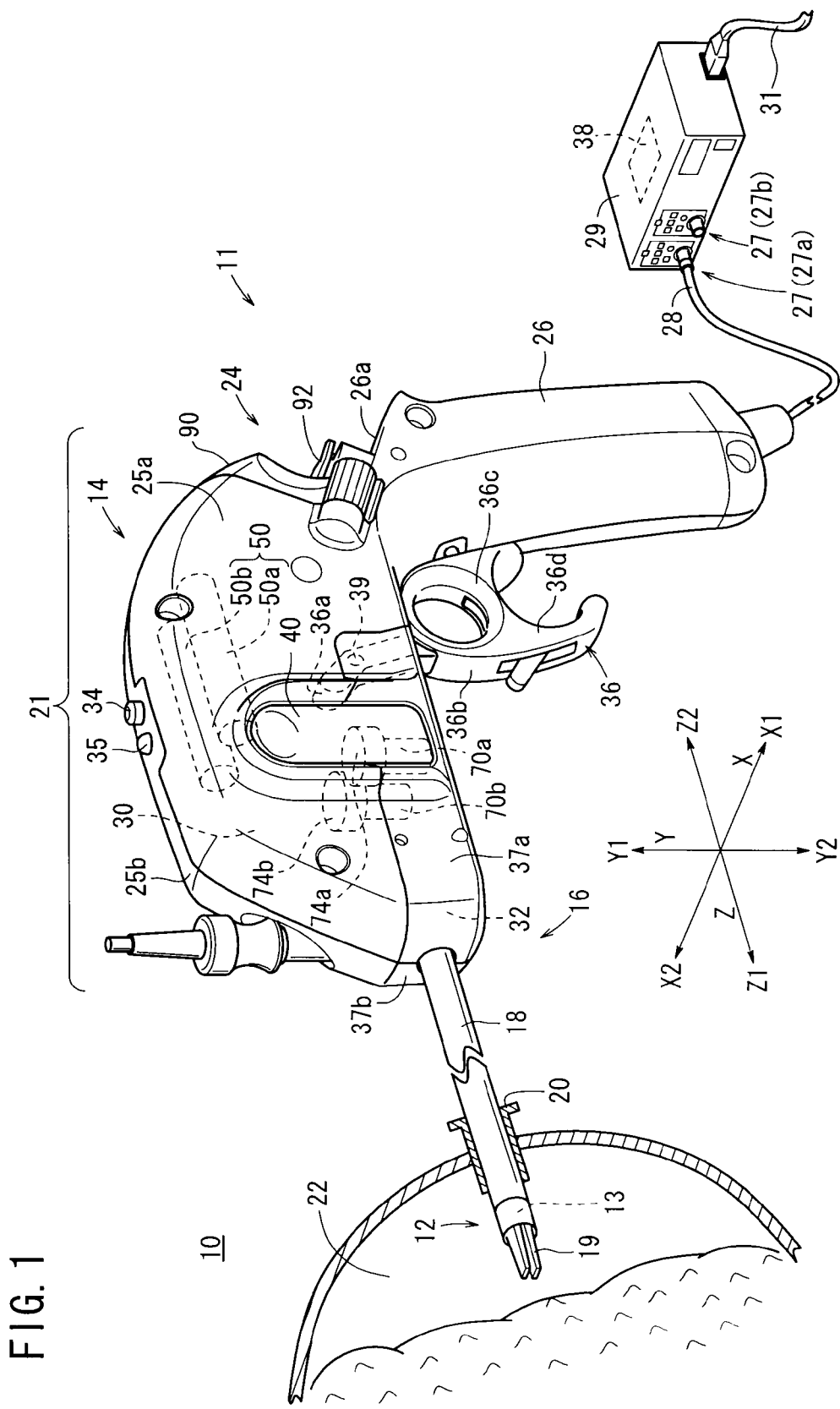
FIG. 1 is a perspective view of a medical manipulator system according to an embodiment of the present invention.

A medical manipulator system (hereinafter referred to as "manipulator system") according to a preferred embodiment of the present invention will be described below with reference to the accompanying drawings. Like or corresponding parts are denoted by like or corresponding reference characters throughout the views.

First, an overall arrangement of a manipulator system 10 according to an embodiment of the present invention will be described below with reference to FIG. 1. As shown in FIG. 1, the manipulator system 10 comprises a manipulator 11 that serves as a medical instrument, which is typically used by a surgeon (operator) for gripping or touching a portion of a living body with a distal-end working unit 12 on the distal end in order to perform a certain treatment. The manipulator system 10 further includes a controller 29 electrically connected to the manipulator 11 by a cable 28. The manipulator 11 includes a body 21, a shaft 18 extending from the body 21, and the distal-end working unit 12, which is mounted on the distal end of the shaft 18.

In the following description, transverse directions of the manipulator 11, which is in the attitude shown in FIG. 1, shall be referred to as X directions, vertical directions of the manipulator 11 shall be referred to as Y directions that are perpendicular to the X directions, and longitudinal directions of the shaft 18 shall be referred to as Z directions that are perpendicular to the X and Y directions. Among the X directions, the leftward direction is referred to as an X1 direction, whereas the rightward direction is referred to as an X2 direction. Among the Y directions, the upward direction is referred to as a Y1 direction, whereas the downward direction is referred to as a Y2 direction. Among the Z directions, the forward direction toward the front end of the shaft 18 is referred to as a Z1 direction, whereas the rearward direction toward the rear end of the shaft 18 is referred to as a Z2 direction.

Unless otherwise noted, these directions represent directions of the manipulator 11 when the manipulator is in a reference or neutral posture. Definitions of the above directions are for illustrative purposes only. The manipulator 11 can be used in any of various orientations, e.g., the manipulator 11 may be used upside down.

The manipulator 11 comprises an operating unit 14, which is held and operated by hand, and a working unit 16 detachably mounted on the operating unit 14. The operating unit 14, which serves as part of the body 21, has a pair of left and right upper covers 25a, 25b extending in a substantially L shape along the Z1 and Y2 directions, which jointly make up a casing, an actuator 30 housed inside the upper covers 25a, 25b, and a composite input unit (operation input unit) 24, which is operable by hand.

The actuator 30 includes two motors 50a, 50b that operate as a drive source 50 for changing the attitude of the distal-end working unit 12. Drive power from the drive source 50 is mechanically transmitted to the distal-end working unit 12 in order to change the attitude of the distal-end working unit 12.

The operating unit 14 has a master switch 34 and an LED (Light-Emitting Diode) 35, which protrude on upper surfaces of the upper covers 25a, 25b near a crest thereof in the Y1 direction. The LED 35 is spaced from the master switch 34 in the Z1 direction for facilitating easier visual recognition thereof.

The operating unit 14 includes a grip handle 26 that is gripped by hand, which extends in the Y2 direction from a proximal end of the operating unit. The composite input unit 24 is disposed on an upper slanted surface 26a of the grip handle 26. The composite input unit 24 can be turned manually to the left and the right, and tilted independently or together. When the composite input unit 24 is turned to the left or the right and/or tilted, the composite input unit 24 sends a corresponding signal to the controller 29, which controls the actuator 30 in order to change the attitude of the end effector 19.

The working unit 16 has a casing made up from a pair of lower covers 37a, 37b, which are separated symmetrically from each other along the Z directions. The working unit 16 comprises the distal-end working unit 12, a pulley box 32 fixed to the proximal end of the shaft 18 and housed in the lower covers 37a, 37b, and a trigger lever 36 disposed rearwardly of the pulley box 32 and which is pivotally supported on the lower covers 37a, 37b for angular movement about a trigger shaft 39, the axis of which extends in the X directions. The lower covers 37a, 37b, the pulley box 32, and the trigger lever 36 serve as part of the body 21.

The working unit 16 is coupled and fixed to the operating unit 14 by a pair of left and right connection/disconnection levers 40 provided on the operating unit 14. The working unit 16 can be separated from the operating unit 14 when the connection/disconnection levers 40 are opened. Therefore, the working unit 16 can be replaced with another working unit easily at the site of the surgical operation without the need for special tools.

The distal-end working unit 12 comprises an end effector 19, which can be opened and closed by the trigger lever 36, and an attitude changing mechanism 13 for changing the attitude of the end effector 19 based on input actions entered by the composite input unit 24. The end effector 19 may be a gripper for gripping a portion of a living body, a suture needle, or scissors for cutting off a portion of a living body, which can be opened and closed about an axis.

The distal-end working unit 12 and the shaft 18 have small diameters and can be inserted into a body cavity 22 through a tubular trocar 20, which is placed in the abdominal region or the like of a patient. The distal-end working unit 12 can perform various surgical techniques to grip, remove, suture, or ligate (tie-knot) an affected part of a patient's body in the body cavity 22, in response to operation of the composite input unit 24 and the trigger lever 36.

The trigger lever 36 comprises an arm 36a pivotally supported by the trigger shaft 39, which is disposed at one end of the lower covers 37a, 37b in the Z2 direction, and a trigger operator 36b, which is connected to an end of the arm 36a in the Y2 direction. The trigger operator 36b includes a finger ring 36c and a substantially arcuate finger rest 36d connected to an end of the finger ring 36c in the Y2 direction.

The end effector 19 is opened and closed when forces, which are produced when the trigger lever 36 is manually operated, i.e., pushed and pulled, are mechanically transmitted to the end effector 19. More specifically, the working unit 16 houses therein a power transmitting mechanism comprising rods, wires, (power transmitting members), pulleys, etc. When the trigger lever 36 is pushed and pulled, movement thereof is converted by the power transmitting mechanism into opening and closing movements of the end effector 19.

The attitude changing mechanism 13 is capable of producing rolling movements about a roll axis directed toward the distal end of the shaft 18, i.e., a Z-axis along the Z direction when the manipulator 11 is in a neutral posture, and also of producing yawing movements (tilting movements) about a yaw axis, i.e., a Y-axis along the Y direction. The attitude changing mechanism 13 can produce rolling and yawing movements selectively or simultaneously. Therefore, the distal-end working unit 12 can move along three axes, i.e., can open and close the end effector 19 in addition to producing rolling and yawing movements.

According to the present embodiment, the distal-end working unit 12 changes the attitude of the end effector 19, i.e., produces rolling and yawing movements, when the drive source 50 is energized by the composite input unit 24 operated by the operator, and the drive power generated by the drive source 50 is transmitted mechanically to the distal-end working unit 12. The composite input unit 24, which is disposed on the upper slanted surface 26a of the grip handle 26, comprises a rotary knob 90 and a tilting knob 92. When the rotary knob 90 is rotated to the left or right, the distal-end working unit 12 produces rolling movements. When the tilting knob 92 is tilted, the distal-end working unit 12 produces yawing movements.

Figure 2:
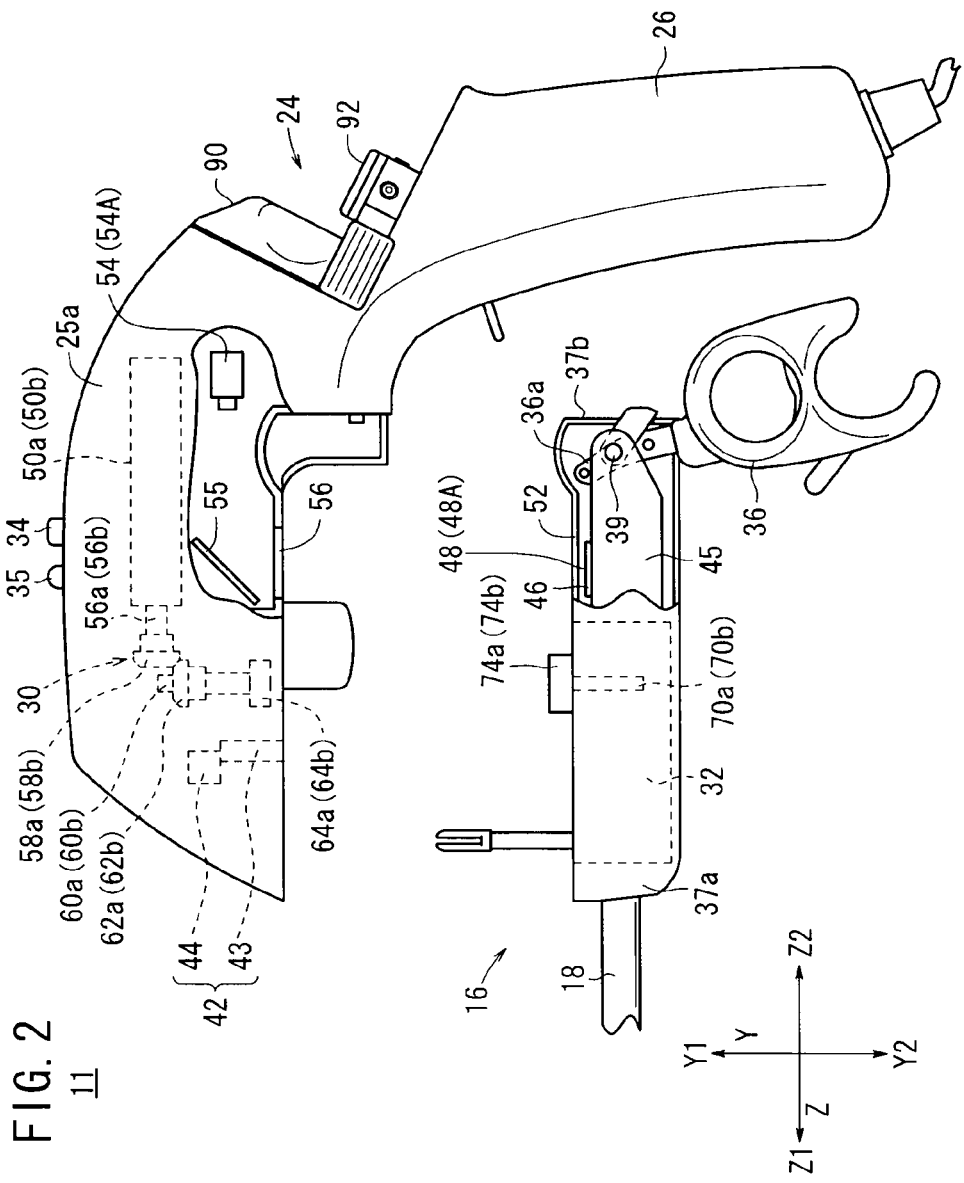
FIG. 2 is a side elevational view, partially omitted from illustration, of a manipulator, with an operating unit and a working unit being separated from each other.

As shown in FIG. 2, the actuator 30 comprises the motors 50a, 50b, two drive bevel gears 58a, 58b fixed to respective output shafts 56a, 56b of the motors 50a, 50b, two driven bevel gears 62a, 62b held in mesh with the respective drive bevel gears 58a, 58b, and two drive shafts 60a, 60b on which the driven bevel gears 62a, 62b are fixedly mounted, respectively. The drive shafts 60a, 60b have engaging bosses 64a, 64b on respective lower ends thereof. The engaging bosses 64a, 64b have wavy cross-sectional shapes, for example. When the motor 50a (50b) is energized, rotational drive power therefrom is transmitted to the engaging boss 64a (64b) through the drive bevel gear 58a (58b), the driven bevel gear 62a (62b), and the drive shaft 60a (60b).

The pulley box 32 houses two pulleys 70a, 70b therein. When the working unit 16 is mounted on the operating unit 14, the pulleys 70a, 70b are aligned coaxially with the drive shafts 60a, 60b, respectively. The pulleys 70a, 70b have respective upper ends, which are connected to engaging sockets 74a, 74b, respectively, protruding from an upper wall of the pulley box 32. The sockets 74a, 74b have wavy cross-sectional shapes, for example. When the working unit 16 is mounted on the operating unit 14, the engaging bosses 64a, 64b engage respectively in the engaging sockets 74a, 74b, due to the wavy cross-sectional shapes thereof, for enabling drive power transmission therethrough. Therefore, rotational drive power from the drive shafts 60a, 60b can be transmitted to the pulleys 70a, 70b through the engaging bosses 64a, 64b and the engaging sockets 74a, 74b. The engaging bosses 64a, 64b and the engaging sockets 74a, 74b may comprise a mutually engaging structure instead of a wavy cross-sectional structure.

Wires, not shown, are trained around the pulleys 70a, 70b, respectively, to serve as power transmitting members. The wires extend through the shaft 18 for transmitting rotational drive power to the attitude changing mechanism 13 of the distal-end working unit 12 (see FIG. 1). Rotational drive power from the drive shafts 60a, 60b can be transmitted through the pulleys 70a, 70b and the wires to the attitude changing mechanism 13, which changes the attitude of the end effector 19.

The mechanism for converting operating actions performed using the trigger lever 36 into opening and closing movements of the end effector 19, and the mechanism for converting drive power from the drive source 50 into movements for changing the attitude of the end effector 19 may be the same as the mechanisms disclosed in Japanese Laid-Open Patent Publication No. 2008-104855 and Japanese Laid-Open Patent Publication No. 2009-106606.

The operating unit 14 includes a mount/dismount detecting mechanism 42 for detecting when the working unit 16 has been mounted on or dismounted from the operating unit 14. The mount/dismount detecting mechanism 42 comprises a detection shaft 43 that functions as a sensor dog, and a detector 44 for detecting an upper end of the detection shaft 43. The detection shaft 43 is movably supported in the casing of the operating unit 14 for movement in the Y directions. The detection shaft 43 normally is biased resiliently by a helical spring, not shown, to move downwardly (FIG. 2) in the Y2 direction, and is retained in place by a snap ring, not shown.

The detector 44 may be a photosensor comprising a light-emitting device and a light-detecting device, which are disposed so as to face each other, for example. When the detection shaft 43 moves into position between the light-emitting device and the light-detecting device, thereby blocking the light path therebetween, the detector 44 detects the detection shaft 43. When the working unit 16 is mounted on the operating unit 14, the detection shaft 43 is pushed in the Y1 direction by the working unit 16 until the upper end thereof is detected by the detector 44. Based on a signal from the detector 44, the controller 29 recognizes that the working unit 16 has been mounted on the operating unit 14.

Between the pulley box 32 and the arm 36a, there is disposed a pair of support plates 45 supporting respective opposite ends of the trigger shaft 39. An ID indication plate 46 extends between and is supported by the support plates 45. The ID indication plate 46 bears an ID holder 48 on an upper surface thereof for holding various items of information of the working unit 16. The ID holder 48 carries a barcode (indicating means) 48A for indicating an image pattern, which is representative of the contents of items of information of the working unit 16. The barcode 48A is exposed on the upper surface of the working unit 16 through a recess 52, which is defined in upper walls of the lower covers 37a, 37b.

The barcode 48A may be a one-dimensional barcode, comprising an array of alternate white and black stripes having different widths, or a two-dimensional matrix barcode such as a QR code (registered trademark), comprising white and black areas arranged in a square pattern. The barcode 48A contains information representative of individual identifying information (ID), specifications, a time stamp (date of manufacture, etc.), a serial number, and a preset limit usage count for the working unit 16. The individual identifying information carried by the barcode 48A comprises a unique value for identifying the working unit 16 among other similar working units.

The ID holder 48 may alternatively carry a contact or contactless storage element, such as a nonvolatile storage element, for enabling reading of data therefrom and writing of data thereto in a contact or contactless fashion. A contactless storage element may comprise an IC tag, for example. If the ID holder 48 carries such a storage element, the storage element should be resistant to sterilization and cleaning.

The operating unit 14 houses therein an ID detector 54 for detecting the barcode 48A. The ID detector 54 comprises a camera 54A for capturing an image of the barcode 48A. The operating unit 14 includes a window 56, comprising a light-permeable member disposed so as to face the barcode 48A when the working unit 16 is mounted on the operating unit 14. The operating unit 14 also houses therein a mirror 55 for reflecting a light image, which travels from the barcode 48A, through the window 56, and toward the camera 54A. Therefore, the camera 54A captures an image of the barcode 48A, which is reflected from the mirror 55. A plurality of LEDs, not shown, are disposed near the camera 54A for emitting light toward the mirror 55. Light emitted from the LEDs is reflected by the mirror 55 in order to illuminate the barcode 48A. The LEDs are capable of emitting a sufficient amount of light to illuminate the barcode 48A.

Since the barcode 48A is incorporated into the working unit 16, the operating unit 14 and the controller 29 can recognize individual identifying information of the working unit 16 based on the image captured by the camera 54A. Accordingly, the controller 29 can control the motors 50a, 50b appropriately and accurately depending on the type of working unit 16 with the end effector 19, such as a gripper, scissors, or an electrical scalpel.

If the ID holder 48 carries a contact or a contactless storage element, then the operating unit 14 includes a reader/writer for reading data from and writing data to the storage element in a contact or contactless fashion. If the storage element comprises an IC tag, then the reader-writer comprises a transceiver for reading data from and writing data to the IC tag in a contactless fashion using electromagnetic waves.

As shown in FIG. 1, the controller 29 is connected to the cable 28, which extends from the lower end of the grip handle 26. The controller 29 serves to control the manipulator 11 as a whole. Some or all of the functions of the controller 29 may be incorporated in and performed by the operating unit 14. The controller 29 is supplied with electric power from an external power supply, i.e., an AC power supply, through a power cable 31, which can be connected to and disconnected from the controller 29.

The controller 29 has a plurality of connection ports 27, including a first port 27a and a second port 27b in the illustrated embodiment. The cable 28 is electrically connected to the first port 27a. Another manipulator, not shown, can be connected to the second port 27b by a cable. Therefore, the controller 29 can simultaneously control a plurality of manipulators, which are connected to the connection ports 27 independently of each other. The controller 29 may have three or more connection ports 27.

The controller 29 uses the signal generated as a trigger signal by the mount/dismount detecting mechanism 42 at a time when the working unit 16 is mounted on the operating unit 14, for activating the camera 54A and the LEDs to acquire individual identifying information of the working unit 16 from the barcode 48A. More specifically, substantially at the same time that the working unit 16 is mounted on the operating unit 14, the controller 29 activates the camera 54A and the LEDs in order to acquire individual identifying information of the working unit 16 from the barcode 48A. The controller 29 activates the camera 54A and the LEDs in order to acquire individual identifying information of the working unit 16 from the barcode 48A only when the working unit 16 is mounted on the operating unit 14. Before and after the working unit 16 is mounted on the operating unit 14, the controller 29 does not activate the camera 54A and the LEDs. Consequently, the processing burden on the controller 29 and the electric power consumed by the controller 29 are reduced.

The controller 29 includes a usage history holder 38 for holding usage history data of each of the working units 16 that have been mounted on the operating unit 14. The usage history holder 38, which comprises a non-volatile storage medium, stores, as usage history data of each of the working units 16, the number of times that the working unit 16 has been used (usage count), the dates on which the working unit 16 were sterilized, the number of times that the end effector 19 has been opened and closed (opening/closing count), etc.

The controller 29 may be connected as a server to communicate with a host computer 33 (see FIG. 3) through a communication means or network, such as a LAN or the like. In such a case, the usage history holder 38 may be incorporated in the host computer 33. Assuming that the usage history holder 38 is incorporated in the host computer 33, then the usage history holder 38 records a usage history table therein, sends and receives usage history data depending on a requested individual number or numbers (an identification number or numbers) to and from the controller 29 or a plurality of controllers 29 connected by the LAN, and manages the usage history data. The host computer 33 need not necessarily be independent of the controller 29, but may have functions thereof incorporated into the controller 29.

If the ID holder 48 carries a storage element, then the storage element may be used as the usage history holder 38. Therefore, the usage history holder 38 may be provided in any one of the working unit 16, the controller 29, and the host computer 33, and is capable of referring to and rewriting the usage history.

The controller 29 has a function to keep the usage count, which is indicative of the number of times that the working unit 16 has been used, as well as the opening/closing count of the end effector 19. Details of a process for keeping the usage count indicative of the number of times that the working unit 16 has been used, and the opening/closing count of the end effector 19 will be described later on.

As shown in FIG. 3, the manipulator 11 further includes a detecting mechanism 100 for detecting an operational state of the trigger lever 36. The detecting mechanism 100 is constructed so as to detect when the trigger lever 36 has reached a pulled position. More specifically, the detecting mechanism 100 detects when the trigger lever 36 has reached an operative position where a gripper 19A of the end effector 19 becomes closed or substantially closed.

While the working unit 16 is mounted on the operating unit 14, the trigger lever 36 can be operated by the operator selectively into a "pushed position" and a "pulled position". The pushed position refers to a position at which the trigger lever 36 is sufficiently pushed away from the grip handle 26, i.e., a position at the end of a turnable range of the trigger lever 36 in the Z1 direction, or a position near to that position. The pulled position refers to a position at which the trigger lever 36 is sufficiently pulled toward the grip handle 26, i.e., a position at the end of the turnable range of the trigger lever 36 in the Z2 direction, or a position near to that position. In FIG. 3, the trigger lever 36 in the pushed position is shown by solid lines, whereas the trigger lever 36 in the pulled position is shown by the two-dot-and-dash lines.

The detecting mechanism 100 comprises a cam (detection finger) 102 joined to the trigger lever 36 and a detector 104 disposed in the operating unit 14. The cam 102 is fixed to the arm 36a of the trigger lever 36 and projects in the Z2 direction. Thus, the cam 102 is movable in unison with the trigger lever 36. More specifically, when the trigger lever 36 is moved angularly in the longitudinal direction of the manipulator 11 (i.e. in the Z directions) the cam 102 also is moved angularly about the trigger shaft 39. The detector 104 is positioned in the operating unit 14 so as to face the cam 102. By detecting the cam 102, the detector 104 detects when the trigger lever 36 has reached the pulled position.

Figure 4A:
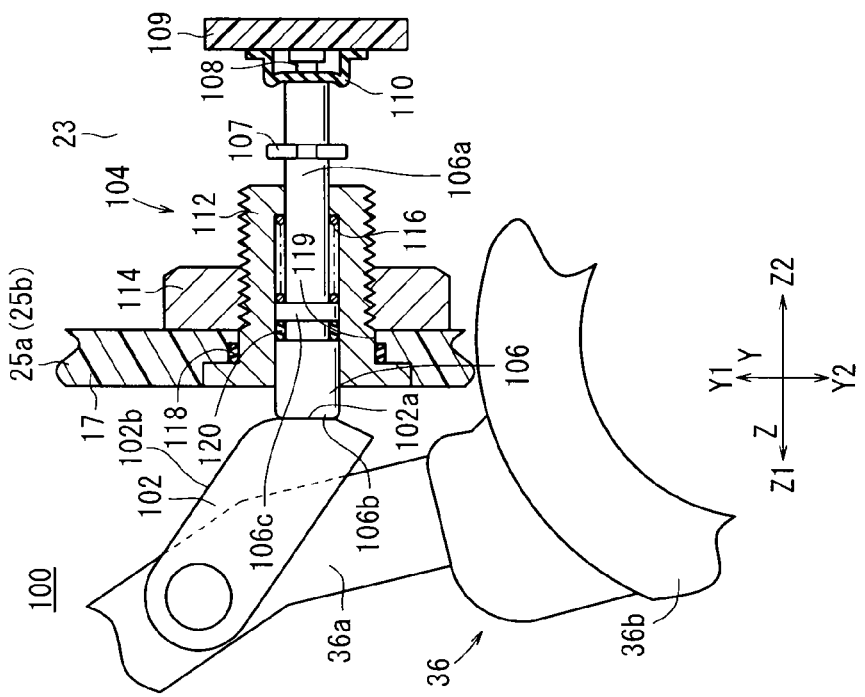
FIG. 4A is an enlarged fragmentary cross-sectional view of a detecting mechanism with a trigger lever being pushed out.
Figure 4B:
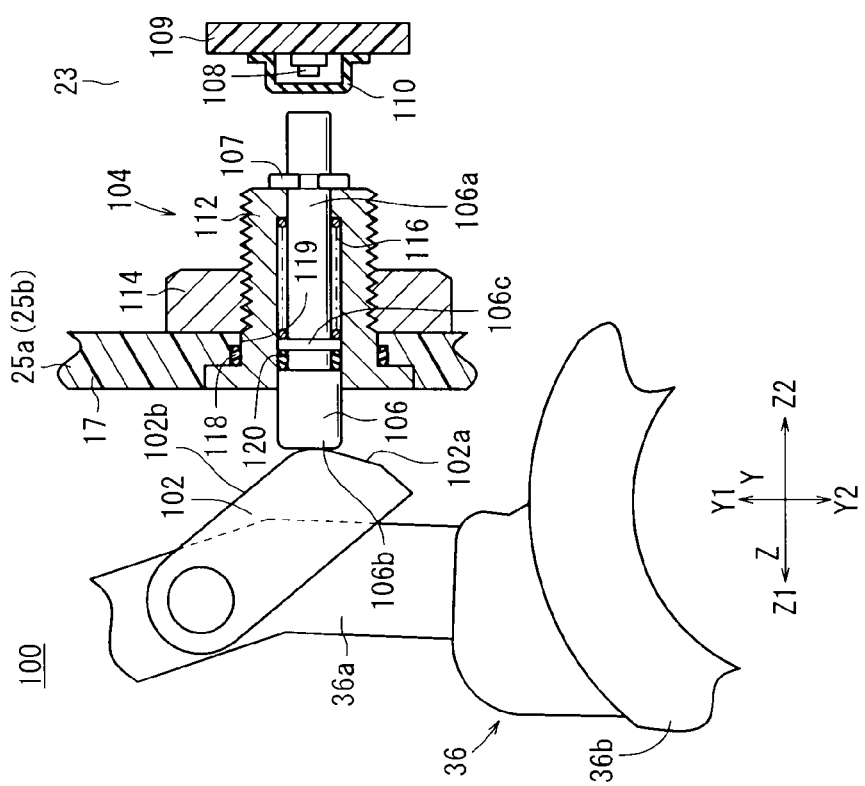

FIG. 4A is an enlarged fragmentary cross-sectional view of the detecting mechanism 100 and nearby components, with the trigger lever 36 being in the pushed position. FIG. 4B is an enlarged fragmentary cross-sectional view of the detecting mechanism 100 and nearby components, with the trigger lever 36 being in the pulled position. As shown in FIGS. 4A and 4B, the detector 104 comprises a trigger rod 106, which can be pushed by the cam 102 so as to move in the Z2 direction, a tubular guide 112 for guiding the trigger rod 106, which is disposed axially and slidably therein, a tactile switch 108 actuatable by the trigger rod 106, a switch board 109 on which the tactile switch 108 is mounted, and a switch cover 110 that covers the tactile switch 108. The switch cover 110 is made from an elastically deformable soft material, such as silicone rubber.

The trigger rod 106 comprises a shank 106a extending through the tubular guide 112 and having an end portion projecting from the tubular guide 112 toward the tactile switch 108, and a head 106b disposed on an opposite end of the shank 106a near the cam 102, and which protrudes from a partition 17 of the upper covers 25a, 25b toward the cam 102. The shank 106a has a flange 106c that projects radially outward therefrom. A seal member 120 in the form of an O-ring is disposed around the shank 106a between the flange 106c and the head 106b. The seal member 120 provides a hermetic seal between the outer circumferential surface of the trigger rod 106 and the inner circumferential surface of the tubular guide 112.

The tubular guide 112 houses therein a helical spring 116, which is disposed around the shank 106a for normally biasing the trigger rod 106 resiliently toward the cam 102. The helical spring 116 has an end abutted against the flange 106c, and another end abutted against an end shoulder of the tubular guide 112. A retainer 107 is fixedly mounted on the outer circumferential surface of the shank 106a outside of the tubular guide 112. The retainer 107 prevents the trigger rod 106 from coming off the tubular guide 112 toward the cam 102.

The tubular guide 112, which is in the shape of a hollow cylinder, is inserted in a hole 119 defined in the partition 17, and is fastened to the partition 17 by a nut 114 screwed over an externally threaded outer circumferential surface of the tubular guide 112 in the upper covers 25a, 25b. A seal member 118 in the form of an O-ring is disposed between the partition 17 and the tubular guide 112. The seal member 118 provides a hermetic seal between the inner circumferential surface of the hole 119 and the outer circumferential surface of the tubular guide 112.

The switch board 109 is electrically connected to the controller 29 by a cable. Signals output from the switch board 109 are transmitted through the cable to the controller 29.

The cam 102 has a cam surface 102a held in abutment with the head 106b of the trigger rod 106. The cam 102 also has a slanted surface 102b contiguous to the cam surface 102a and inclined in the Y2 direction toward the Z2 direction. When the cam 102 is turned counterclockwise about the trigger shaft 39 in FIG. 4A, the cam surface 102a pushes the trigger rod 106 in the Z2 direction against the resilient force of the helical spring 116.

The detector 104 thus constructed operates in the following manner. When the trigger lever 36 is in the pushed position, as shown in FIG. 4A, the cam 102 does not press the trigger rod 106 in the Z2 direction, and hence the trigger rod 106 does not press the tactile switch 108. When the trigger lever 36 is pulled in the Z2 direction from the pushed position to the pulled position, as shown in FIG. 4B, the cam 102 presses the trigger rod 106 in the Z2 direction, and hence the trigger rod 106 presses the tactile switch 108 with the switch cover 110 interposed therebetween. At this time, the tactile switch 108 is triggered to detect that the trigger lever 36 is in the pulled position. The tactile switch 108 outputs a signal representative of the pulled position to the controller 29, which recognizes that the trigger lever 36 is in the pulled position.

The cam 102 has a slanted surface 102b contiguous to the cam surface 102a. The slanted surface 102b allows the working unit 16 to be installed on the operating unit 14, regardless of the angle at which the trigger lever 36 is angularly positioned with respect to the working unit 16 and the operating unit 14. For example, when the working unit 16 is installed on the operating unit 14 while the trigger lever 36 is in the pulled position, the distal end of the trigger rod 106 is brought into contact with the slanted surface 102b of the cam 102, and the trigger rod 106 is pressed in the Z2 direction, thereby triggering the tactile switch 108. Therefore, when the working unit 16 is completely mounted on the operating unit 14, the controller 29 recognizes that the trigger lever 36 is in the pulled position.

In the illustrated embodiment, the detecting mechanism 100 detects when the trigger lever 36 is in the pulled position. However, the detecting mechanism 100 may be arranged to detect when the trigger lever 36 is in the pushed position. Alternatively, the detecting mechanism 100 may be arranged to detect both when the trigger lever 36 is in the pulled position and when the trigger lever 36 is in the pushed position. According to another alternative, the cam 102 may be provided on the trigger operator 36b, and the detector 104 may be provided in the grip handle 26.

The manipulator system 10 with the detecting mechanism 100 manages usage of the working unit 16 in the following manner. Each time that the trigger lever 36 reaches the pulled position or the pushed position, the detector 104 sends a signal to the controller 29, which counts the signal. The controller 29 stores the usage count of the working unit 16 in the usage history holder 38, as usage history data in association with the identification number of the working unit 16. The controller 29 also counts the number of times that the trigger lever 36 has reached the pulled position or the pushed position, and stores a corresponding count as an opening/closing count of the end effector 19 in the usage history holder 38.

Since the detecting mechanism 100 is capable of detecting when the trigger lever 36 reaches the pulled position or the pushed position as an operated state of the trigger lever 36, the manipulator system 10 can recognize and analyze the number of times that the trigger lever 36 has been operated, i.e., the opening/closing count of the end effector 19, as well as how the trigger lever 36 has been used. Based on such an analysis, it is possible to predict the remaining service life of the trigger lever 36, and the mechanism for mechanically transmitting the force produced by the trigger lever 36 when the trigger lever 36 is operated.

The tactile switch 108 of the detector 104 may be replaced with a photosensor comprising a light-emitting device and a light-detecting device. If such a photosensor is employed, then the light-emitting device and the light-detecting device are positioned such that when the trigger lever 36 reaches the pulled position, the trigger rod 106 is placed between the light-emitting device and the light-detecting device, thereby blocking light from the light-emitting device. Therefore, the photosensor can detect when the trigger lever 36 has reached the pulled position.

Figure 5:
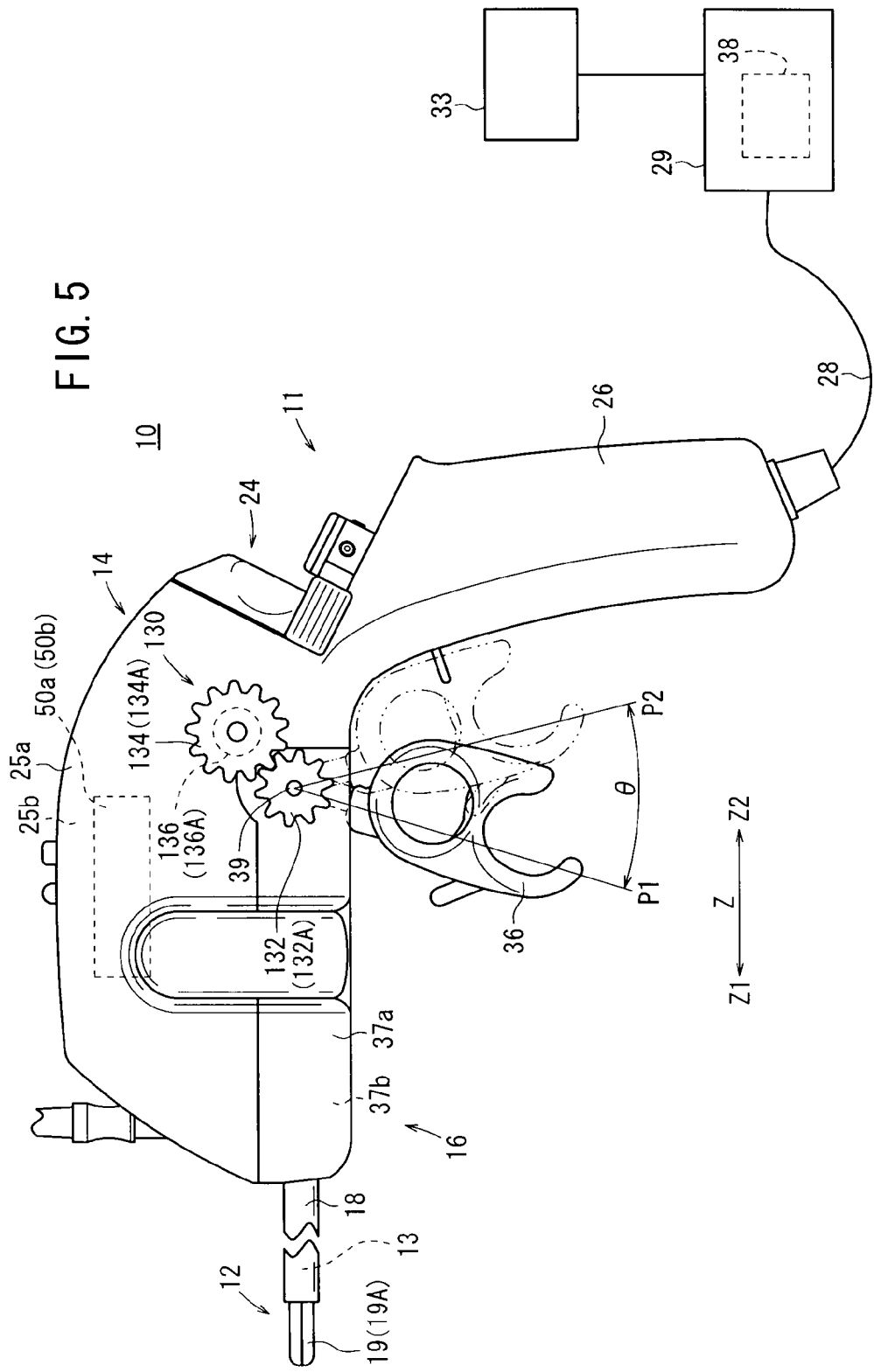
FIG. 5 is a side elevational view, partially omitted from illustration, of a manipulator system having a detecting mechanism according to a modification.
Figure 6:
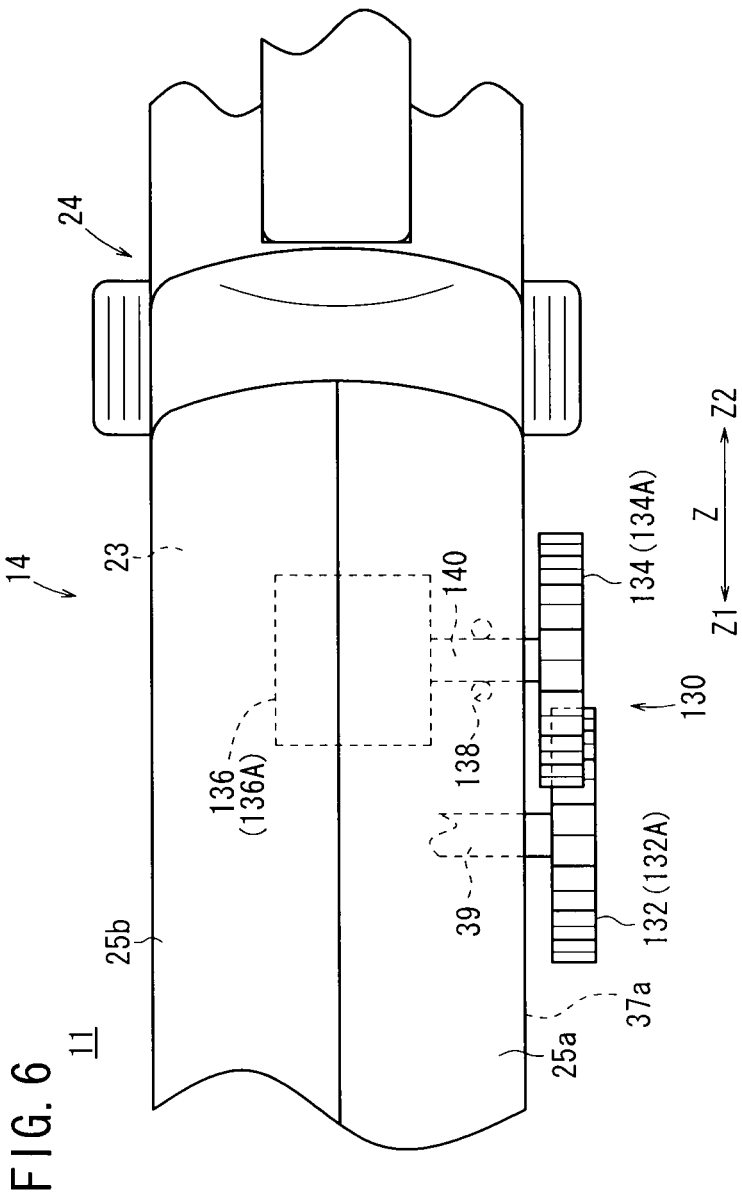
FIG. 6 is a plan view, partially omitted from illustration, of the manipulator system having the detecting mechanism according to the modification.

A detecting mechanism 130 according to a modification will be described below with reference to FIGS. 5 and 6. FIG. 5 is a side elevational view, partially omitted from illustration, of a manipulator system 10 having the detecting mechanism 130 according to the modification, and FIG. 6 is a plan view, partially omitted from illustration, of the manipulator system 10 having the detecting mechanism 130 according to the modification. The detecting mechanism 130 is capable of detecting an angular position of the trigger lever 36 along directions in which the trigger lever 36 is turnable. As shown in FIG. 5, the trigger lever 36 is turnable within an angular range indicated by an angle θ from a pushed position, i.e., a foremost position, P1 in which the trigger lever 36 is turned farthest in the Z1 direction, to a pulled position, i.e., a rearmost position, P2 in which the trigger lever 36 is turned farthest in the Z2 direction.

The detecting mechanism 130 comprises a drive element 132 mounted on the working unit 16 and movable in unison with the trigger lever 36, a driven element 134 mounted on the operating unit 14 and operatively ganged with the drive element 132 when the working unit 16 is mounted on the operating unit 14, and a detector 136 for detecting a position of the driven element 134 along directions in which the trigger lever 36 is turned. In the illustrated modification, the drive element 132 comprises a first gear 132A rotatably mounted on the working unit 16 and having circumferential gear teeth around the axis of the trigger shaft 39. The driven element 134 comprises a second gear 134A rotatably mounted on the operating unit 14 and held in mesh with the first gear 132A when the working unit 16 is mounted on the operating unit 14. The detector 136 comprises a rotational angle detector 136A for detecting a rotational angle of the second gear 134A.

As shown in FIG. 6, the first gear 132A is angularly rotatably mounted on an outer side of the lower cover 37a of the working unit 16, for angular movement in unison with the trigger lever 36. More specifically, the first gear 132A is fixed to the trigger shaft 39, which is angularly rotatable in unison with the trigger lever 36. When the trigger lever 36 is turned in longitudinal directions of the operating unit 14 and the working unit 16, i.e., in directions indicated by the arrow Z, the first gear 132A is turned in unison with the trigger lever 36 about the axis of the trigger shaft 39. In FIGS. 5 and 6, the first gear 132A is illustrated as having gear teeth disposed fully therearound. However, the first gear 132A may have gear teeth disposed partially therearound, as long as such gear teeth are capable of meshing with the gear teeth of the second gear 134A within the full turnable range of the trigger lever 36.

The second gear 134A is angularly rotatably mounted on an outer side of the upper cover 25a of the operating unit 14. The rotational angle detector 136A is disposed in an inner space 23 jointly defined by the upper covers 25a, 25b. The second gear 134A is coupled to the rotational angle detector 136 by a shaft 140 that extends through the upper cover 25a.

A seal member 138 in the form of an O-ring is disposed around the shaft 140 in the upper cover 25a, in order to provide a hermetic seal for preventing fluids and dust from entering along the shaft 140 into the inner space 23.

The rotational angle detector 136A may comprise a rotary encoder, a potentiometer, a resolver, or the like. If the rotational angle detector 136A comprises a rotary encoder, then the rotary encoder may be either an incremental encoder or an absolute encoder. The rotational angle detector 136A is electrically connected to the controller 29 by the cable 28. Signals output from the rotational angle detector 136A are transmitted through the cable 28 to the controller 29.

When the trigger lever 36 is turned about the axis of the trigger shaft 39 through a certain operating angle, the first gear 132A is turned in unison with the trigger lever 36 about the axis of the trigger shaft 39. As the first gear 132A is turned, the second gear 134A, which is held in mesh therewith, also is turned through a corresponding rotational angle, which is detected by the rotational angle detector 136A. Therefore, the rotational angle detector 136A detects the operating angle through which the trigger lever 36 has been turned. The rotational angle detector 136A outputs a signal representative of the detected operating angle. The signal is transmitted through the cable 28 to the controller 29. Based on the signal from the rotational angle detector 136A, the controller 29 calculates the operating angle through which the trigger lever 36 has been turned.

If the rotational angle detector 136A comprises an incremental encoder, then the rotational angle detector 136A only outputs pulses depending on a change in the rotational angle of the trigger lever 36, but is incapable of directly detecting the absolute rotational angle of the trigger lever 36. However, since the angular movable range (maximum rotational angle) θ of the trigger lever 36 is known, it is possible to estimate the absolute rotational angle of the trigger lever 36 from the angular range detected when the manipulator 11 is in use. Therefore, if the rotational angle detector 136A comprises an incremental encoder, the controller 29 estimates (calculates) the absolute rotational angle of the trigger lever 36 based on the angular movable range θ of the trigger lever 36 and an angular range detected by the rotational angle detector 136A. Since the absolute rotational angle of the trigger lever 36 is estimated from a detected signal from the incremental encoder, the operating angle of the trigger lever 36 can be detected with a simple arrangement.

While the manipulator 11 of the manipulator system 10, which incorporates the detecting mechanism 130 therein, is in use, the operating angle of the trigger lever 36 is detected within each given sampling time, and is stored in the usage history holder 38 as usage history data in association with the identification number of the working unit 16. More specifically, the manipulator system 10 is capable of detecting and storing the usage count of the working unit 16 (the opening/closing count of the end effector 19) as well as the usage state thereof. Based on the usage count of the working unit 16 and the usage state thereof, it is possible to predict the remaining service life of the trigger lever 36 and the mechanism for mechanically transmitting the force produced by the trigger lever 36 when the trigger lever 36 is operated. In particular, because the detecting mechanism 130 detects the operating angle of the trigger lever 36, the detecting mechanism 130 according to the modification makes it possible to recognize the usage state of the trigger lever 36 in greater detail, and to predict, with better reliability than the detecting mechanism 100, the remaining service life of the trigger lever 36 and the mechanism for mechanically transmitting the force produced by the trigger lever 36 when the trigger lever 36 is operated.

The manipulator system 10 is constructed as a system capable of appropriately collecting, updating, and managing usage history data of the working unit 16. When the operating unit 14 is connected to the controller 29 and the working unit 16 is installed on the operating unit 14 while the manipulator system 10 is in operation, the controller 29 recognizes installation of the working unit 16, and outputs a control command to the camera 54A to acquire individual identifying information of the working unit 16. In response to the control command, the camera 54A acquires individual identifying information of the working unit 16 from the barcode 48A, analyzes the acquired individual identifying information, and transmits the result of such analysis to the controller 29.

Based on the individual identifying information of the working unit 16, the controller 29 refers to the individual identifying information and the usage history data stored in the usage history holder 38 of the controller 29, and determines whether or not the working unit 16 is usable. More specifically, if the usage count of the working unit 16 is equal to or smaller than the limit usage count (preset count) of the working unit 16, then the controller 29 judges that the working unit 16 is usable. However, if the usage count of the working unit 16 exceeds the limit usage count of the working unit 16, then the controller 29 judges that the working unit 16 is not usable.

If the controller 29 judges that the working unit 16 is usable, then the controller 29 increments the usage count of the working unit 16 and updates the usage history data. When the composite input unit 24 of the manipulator 11, which incorporates therein the working unit 16 that has been judged as being usable, is operated in order to enter an operation command, the controller 29 controls the motors 50a, 50b based on the operation command in order to actuate the distal-end working unit 12. If the controller 29 judges that the working unit 16 is not usable, i.e., if the usage count of the working unit 16 exceeds the limit usage count of the working unit 16, then the controller 29 cancels any operation commands that are entered from the composite input unit 24, thereby disabling the working unit 16. Therefore, even if the operator operates the composite input unit 24, the motors 50a, 50b are not energized, and the distal-end working unit 12 is not actuated.

The controller 29 judges the start and end of a surgical case based on the manner in which the working unit 16 is mounted and dismounted, and based on the times at which the working unit 16 is mounted and dismounted. The controller 29 then produces a usage count of the working unit 16 according to certain usage count rules. According to the usage count rules, the maximum usage time of each working unit 16 per usage event is limited using a first preset time. According to the usage count rules, furthermore, switching between surgical cases (the end of a surgical case) is judged using a second preset time and a third preset time. The usage count rules, using the first preset time, the second preset time, and the third preset time, will be described below.

First, the usage count rule using the first preset time will be described below with reference to FIG. 7.

When the working unit 16 is used in a surgical case, wherein the actual surgical operation continues for an extended period of time, if usage of the working unit 16 is regarded as a single usage event, then the working unit 16 may possibly suffer from a durability problem. According to the usage count rule using the first preset time, usage of the working unit 16 in the first preset time, e.g., five hours, is regarded as one usage event, and the usage count of the working unit 16 is counted accordingly. More specifically, each time that a surgical case is started when a given usage starting condition for the working unit 16 is satisfied, the usage count of the working unit 16 is incremented. If the working unit 16 is used for a period of time beyond the first preset time during one surgical case, then the usage count of the working unit 16 is incremented each time that the period of time in which the working unit 16 has been used exceeds the first preset time.

The "usage starting condition" referred to above is a condition for judging that the working unit 16 starts to be used. More specifically, the usage starting condition is satisfied when the working unit 16 is operated, i.e., when the operator operates the composite input unit 24 to energize the motors 50a, 50b and to actuate the distal-end working unit 12 for the first time after a "surgical case ending condition", to be described later, is satisfied, or after the usage count of the working unit 16 has been incremented.

A "surgical case starting condition" is a condition for judging the start of one surgical case according to a certain rule. More specifically, the surgical case starting condition is satisfied when the usage starting condition for the working unit 16 is satisfied for the first time after the surgical case ending condition is satisfied, or when the manipulator system 10 is newly used.

The "surgical case ending condition" is a condition for judging the end of one surgical case according to a certain rule. The second preset time and the third preset time are used for determining whether or not the surgical case ending condition has been satisfied.

The term "one surgical case" referred to above implies a single unit of a surgical operation to be performed as a medical treatment using the manipulator 11, i.e., a single operation.

Figure 7:
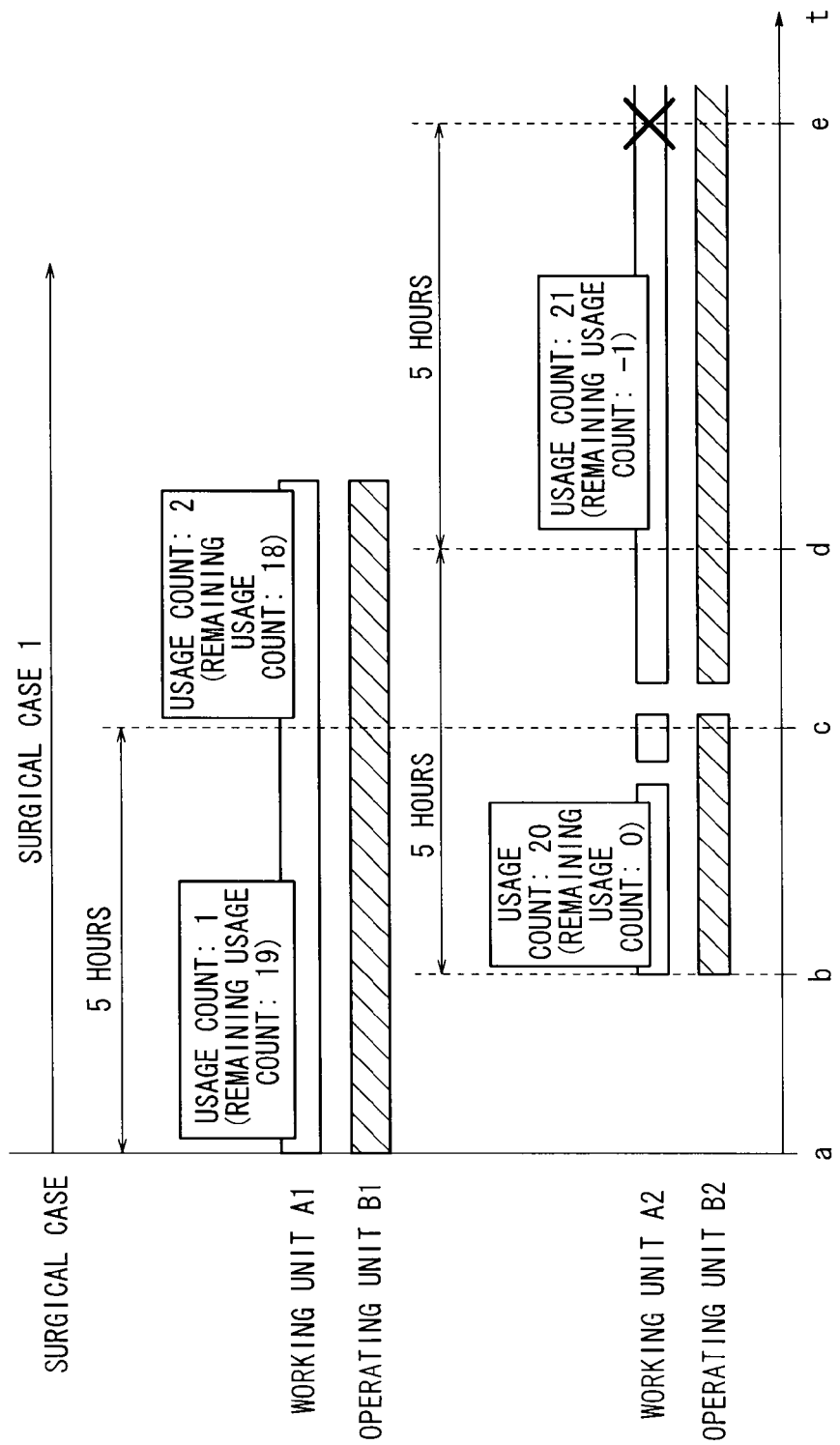
FIG. 7 is a diagram illustrative of a usage count rule based on a first preset time.

In FIG. 7, the horizontal axis represents time, and horizontal bars represent how operating units B1, B2, each identical to the operating unit 14, are connected to the controller 29, as well as how working units A1, A2, each identical to the working unit 16, are connected to the operating units B1, B2. More specifically, the blank bars represent periods of time during which the working units A1, A2 are connected to the operating units B1, B2, whereas the hatched bars represent periods of time during which the operating units B1, B2 are connected to the controller 29.

An example of a process for counting usage counts of the working units A1, A2 using the first preset time will be described below. It is assumed that the first preset time is five hours and the limit usage count (preset count) is 20. As shown in FIG. 7, at time "a", the operating unit B1 is connected to the controller 29 and the working unit A1 is installed on the operating unit B1. The controller 29 then recognizes individual identifying information of the working unit A1. Even if the operating unit B1 has been connected solely to the controller 29 prior to time "a", and the working unit A1 then is installed on the operating unit B1 at time "a", the controller 29 similarly recognizes individual identifying information of the working unit A1 at that time.

When the operator operates the composite input unit 24 for the working unit A1 in order to enter an operation command, the usage starting condition for the working unit A1 is satisfied, and the surgical case starting condition also is satisfied. At this time, the controller 29 judges that Surgical Case 1 has started, and increments the usage count of the working unit A1. The controller 29 also monitors a period of usage time from a time when the usage starting condition for the working unit A1 is satisfied, i.e., starts to count down five hours, based on a timer function. It is assumed that the usage count of the working unit A1 is 1, i.e., that the remaining number of times that the working unit A1 can be used (remaining usage count) is 19.

Thereafter, at time "b", the operating unit B2 is connected to the controller 29 and the working unit A2 is installed on the operating unit B2. The controller 29 recognizes individual identifying information of the working unit A2. When the operator operates the composite input unit 24 for the working unit A1 in order to enter an operation command, the usage starting condition for the working unit A2 is satisfied, and the controller 29 increments the usage count of the working unit A2. It is assumed that the usage count of the working unit A1 is 20, i.e., the remaining usage count of the working unit A1 is 0. When the usage starting condition for the working unit A2 is satisfied (at time "b"), Surgical Case 1 has already started because the surgical case starting condition therefor has been satisfied, however, the surgical case ending condition for Surgical Case 1 is not satisfied. Consequently, the surgical case starting condition is not satisfied again, even though the usage starting condition for the working unit A2 is satisfied.

At time "c", because the usage time of the working unit A1 reaches five hours (the first preset time), the controller 29 increments the usage count of the working unit A1. As a result, the usage count of the working unit A1 becomes 2, i.e., the remaining usage count of the working unit A1 becomes 18. At time "c", since the usage time of the working unit A2 does not reach five hours, the controller 29 does not increment the usage count of the working unit A2.

At time "d", the usage time of the working unit A2 reaches five hours, and the controller 29 increments the usage count of the working unit A2. As a result, the usage count of the working unit A2 becomes 21, which exceeds the limit usage count. If the working unit A2 is immediately prevented from being used at this time, however, the surgical operation will be interrupted, adversely affecting the patient. Therefore, even though the usage count of the working unit A2 exceeds the limit usage count due to the fact that the usage time thereof during Surgical Case 1 exceeds the first preset time, the working unit A2 is allowed to operate continuously for a special preset time (ten hours in FIG. 7) longer than the first preset time. Accordingly, the surgical operation can be performed smoothly, since the working unit A2 will not be forcibly disabled during the surgical operation. The special preset time may be of a length corresponding to a maximum time, which is expected to be required for Surgical Case 1 to be completed.

At time "e", the usage time of the working unit A2 reaches ten hours (the special preset time), and the controller 29 disables the working unit A2. More specifically, even when the operator operates the composite input unit 24 of the operating unit B2 on which the working unit A2 has been mounted after time "e", the controller 29 cancels any operation commands entered from the composite input unit 24, thereby maintaining the motors 50a, 50b in a deenergized state.

As described above, the manipulator system 10 increments the usage count of the working unit 16 based on the manner in which the working unit 16 is mounted and dismounted, and the times at which the working unit 16 is mounted and dismounted. If the usage count of the working unit 16 exceeds the preset limit usage count, then the manipulator system 10 disables the working unit 16 and prevents operation thereof. Therefore, even when the operator operates the composite input unit 24, the actuator 30 is not energized. In other words, actions performed on the composite input unit 24 are canceled so as to maintain the distal-end working unit 12 including the end effector 19 in a disabled state. In this manner, the working unit 16, the usage count of which has reached the limit usage count, is forcibly made unusable.

During one surgical case, the manipulator system 10 increments the usage count of the working unit 16 each time that the usage time exceeds the first preset time. Consequently, the working unit 16 is prevented from being used infinitely and hence from experiencing a durability problem.

The usage count of the working unit 16 may reflect a parameter representative of the service life of the working unit 16, i.e., a parameter that increases as the working unit 16 is used. For example, such a parameter may be represented by an opening/closing count of the end effector 19, i.e., the number of times that the trigger lever 36 is operated, because when the end effector 19 is opened and closed, a load is imposed on the drive system for operating the end effector 19, thereby adversely affecting the service life of the working unit 16.

The parameter representative of the service life of the working unit 16 may also be a parameter of a different type, or a parameter based on a combination of parameters of different types, apart from the opening/closing count of the end effector 19. For example, the parameter representative of the service life of the working unit 16 may be a parameter, which is generated by detecting the number of times that the attitude changing mechanism 13 has produced rolling and yawing movements, positions and speeds of the attitude changing mechanism 13 while the attitude changing mechanism 13 produces rolling and yawing movements, and currents supplied to the motors 50a, 50b, weighting such values, and calculating the weighted values.

As described above, the manipulator system 10 counts the opening/closing count of the end effector 19 by detecting the operated state of the trigger lever 36 via the detecting mechanisms 100, 130 (see FIGS. 4A, 5). Consequently, the manipulator system 10 is capable of counting the usage count of the working unit 16 while reflecting a parameter that increases as the working unit 16 is used. The manipulator system 10 can measure the number of times that the attitude changing mechanism 13 has produced rolling and yawing movements, by storing the operating actions performed using the composite input unit 24 in the usage history holder 38. The manipulator system 10 can detect positions and speeds of the attitude changing mechanism 13 while the attitude changing mechanism 13 produces rolling and yawing movements based on detected signals from encoders (not shown) associated with the motors 50a, 50b, and is capable of storing the detected positions and speeds in the usage history holder 38. If the operating unit 14 includes sensors for detecting currents supplied to the motors 50a, 50b, then the manipulator system 10 can detect and store such currents in the usage history holder 38.

The usage count of the working unit 16, which reflects a parameter that increases as the working unit 16 is used, is counted in the following manner. The controller 29 measures or calculates the parameter that increases as the working unit 16 is used, e.g., the opening/closing count of the end effector 19. Then, when the parameter reaches a reference value determined depending on the usage count of the working unit 16 in one surgical case, the controller 29 increments the usage count of the working unit 16, even before the usage time of the working unit 16 has reached the first preset time.

More specifically, if the parameter that increases as the working unit 16 is used is denoted by P, the opening/closing count of the end effector 19 at which the service life of the working unit 16 ends (hereinafter referred to as "stress level") is represented by Q, the limit usage count for the working unit 16 is represented by $N_{max}$, and the present usage count of the working unit 16 is represented by N, then the controller 29 increments the usage count of the working unit 16 when the following equation (1) is satisfied:

$$P = Q \times (N/N_{max}) \quad (1)$$

For example, if the stress level is 1000, the limit usage count $N_{max}$ for the working unit 16 is 20, and the present usage count N of the working unit 16 is 6, then since $Q \times (N/N_{max}) = 300$, the controller 29 increments the usage count of the working unit 16 when the opening/closing count of the end effector 19, i.e., parameter P, reaches 300.

Figure 8:
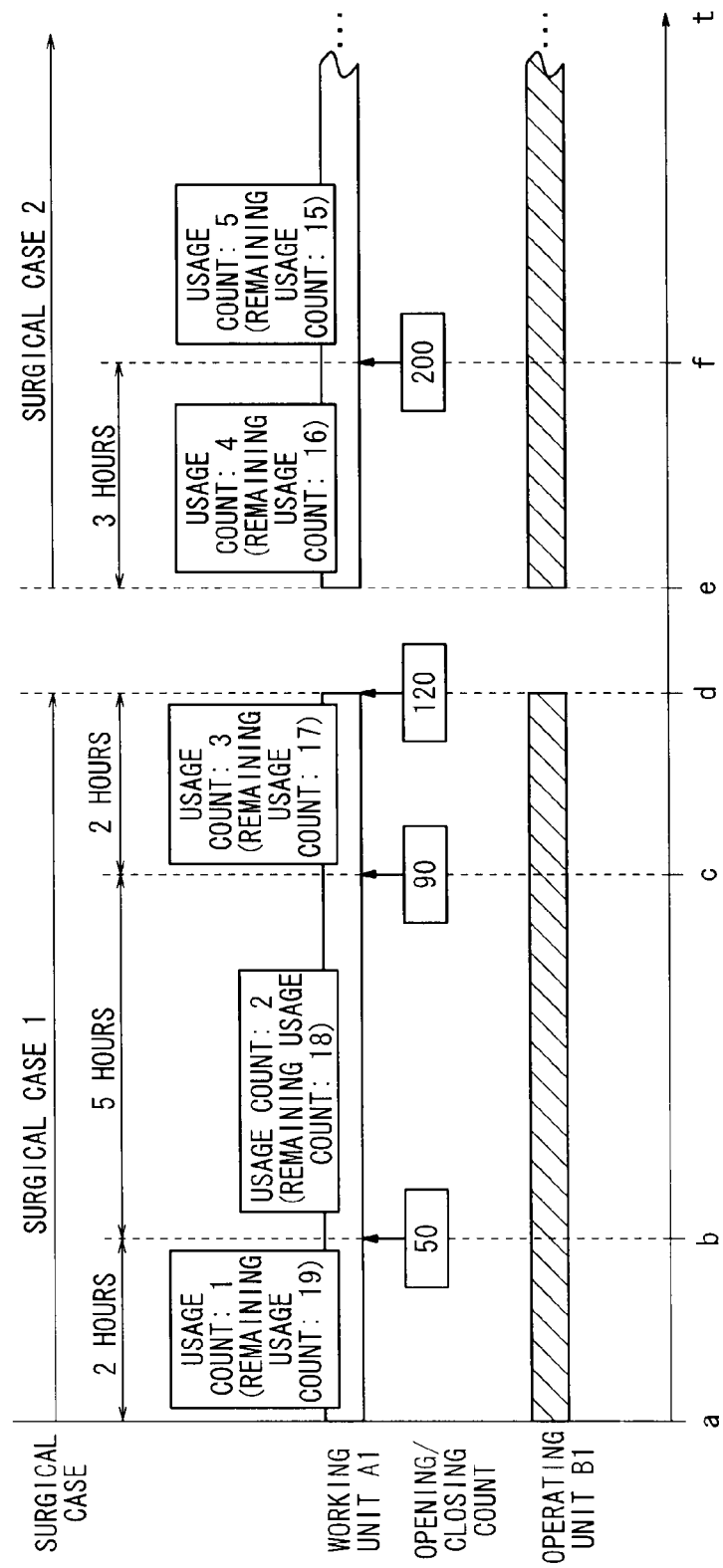
FIG. 8 is a diagram illustrative of a usage count rule that takes into account the number of times that an end effector has been opened and closed.

A specific example of a process of incrementing the usage count of the working unit 16 using the above parameter P will be described below with reference to FIG. 8. It is assumed that the first preset time is five hours, the stress level Q is 1000, and the limit usage count $N_{max}$ for the working unit 16 is 20. As shown in FIG. 8, at time "a", the usage starting condition for the working unit A1 is satisfied, Surgical Case 1 starts, and the usage count of the working unit A1 is 1, i.e., the remaining usage count of the working unit A1 is 19.

At time "b", the usage time of the working unit A1 has not yet reached the first preset time. However, since the opening/closing count of the end effector 19, i.e., parameter P, has reached 50 and $Q \times (N/N_{max}) = 1000 \times (1/20) = 50$, the controller 29 increments the usage count of the working unit A1. As a result, the usage count of the working unit A1 becomes 2, i.e., the remaining usage count of the working unit A1 becomes 18. At this time, counting down of the first preset time is stopped, and the time therefor is reset and restarted.

At time "c", the usage time of the working unit A1 reaches five hours (the first preset time). The controller 29 increments the usage count of the working unit A1. As a result, the usage count of the working unit A1 becomes 3, i.e., the remaining usage count of the working unit A1 becomes 17. Surgical Case 1 ends at time "d".

At time "e", the working unit A1 starts to be used for the fourth time, i.e., the remaining usage count of the working unit A1 is 16, and Surgical Case 2 starts. In this case, $Q \times (N/N_{max}) = 200$. The opening/closing count of the end effector 19, i.e., parameter P, reaches 200 at time "f" during Surgical Case 2. The controller 29 increments the usage count of the working unit A1. As a result, the usage count of the working unit A1 becomes 5, i.e., the remaining usage count of the working unit A1 becomes 15.

As described above, since the usage count of the working unit 16 is incremented while reflecting the opening/closing count of the end effector 19, which represents an actual manner in which the working unit 16 is used, the time at which the working unit 16 becomes disabled based on the usage count thereof is optimized.

A usage count rule using the second preset time will be described below. The second preset time is applied while the first preset time also is being applied.

When the surgical case switches to another surgical case, the operating unit 14 may be disconnected from the controller 29 for a temporary period of time, e.g., 10 minutes or longer, in order to perform sterilization thereof, even though the controller 29 remains energized. Alternatively, if the operating unit 14 is replaced with another operating unit 14 due to an error, the operating unit 14 is highly likely to be replaced within a short period of time, e.g., 10 minutes or shorter. When the operating unit 14 remains disconnected from the controller 29 for more than the second preset time, e.g., 10 minutes, while the controller 29 remains energized, it is judged that the surgical case has been switched to another surgical case, or that the present surgical case has finished. The second preset time is shorter than the first preset time.

While the controller 29 remains energized, the operating unit 14 is disconnected from the controller 29, and thereafter, the same operating unit 14 or another operating unit 14 is reconnected to the controller 29. If the operating unit 14 is connected to the controller 29 within the second preset time after the operating unit 14 was disconnected from the controller 29, then the controller 29 judges that the surgical case has not been switched to another surgical case. At this time, the controller 29 does not increment the usage count of the connected working unit 16. If the operating unit 14 is connected to the controller 29 beyond the second preset time after the operating unit 14 has been disconnected from the controller 29, then the controller 29 judges that the surgical case has been switched to another surgical case, and increments the usage count of the connected working unit 16 accordingly.

A specific example of a process of incrementing the usage count of the working unit 16, using the first preset time and the second preset time, will be described below with reference to FIG. 9. It is assumed that the first preset time is five hours, the second preset time is 10 minutes, and the limit usage count for the working unit 16 is 20. The symbols and graphic patterns used in FIG. 9 have the same meanings as those used in FIG. 7.

Figure 9:
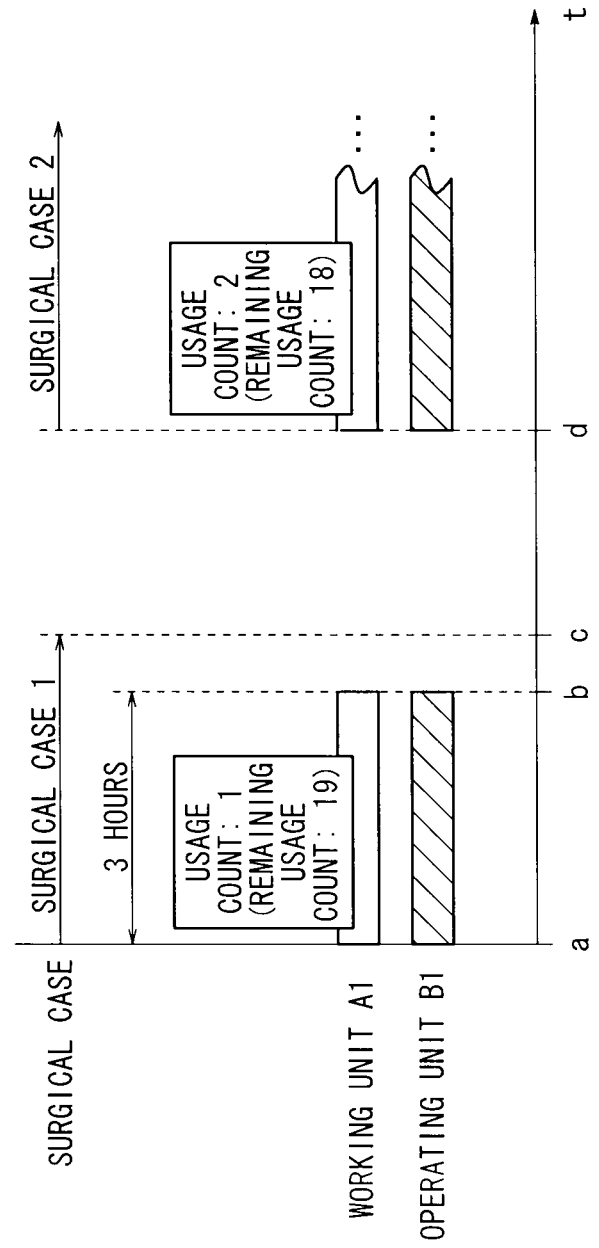
FIG. 9 is a diagram illustrative of switching between surgical cases based on a second preset time.

As shown in FIG. 9, at time "a", the operating unit B1 is connected to the controller 29, and the working unit A1 is installed on the operating unit B1. At the same time, the controller 29 recognizes individual identifying information of the working unit A1. When the operator operates the composite input unit 24 of the operating unit B1 in order to enter an operation command, the usage starting condition for the working unit A1 is satisfied. The controller 29 judges that Surgical Case 1 has started, counting down of the first preset time (five hours) is started, and the controller 29 increments the usage count of the working unit A1. As a result, it is assumed that the usage count of the working unit A1 becomes 1, i.e., the remaining usage count of the working unit A1 becomes 19.

At time "b", the operating unit B1 with the working unit A1 mounted thereon is disconnected from the controller 29. Since an operating unit is not connected to the controller 29, counting down of the second preset time (10 minutes) by the controller 29 is started. At time "c", which is 10 minutes later than time "b", since an operating unit still is not connected to the controller 29, the controller 29 judges that Surgical Case 1 has finished, according to a rule based on the second preset time.

At time "d", the operating unit B1 is connected to the controller 29, and the working unit A1 is installed on the operating unit B1. At the same time, the controller 29 recognizes individual identifying information of the working unit A1. When the operator operates the composite input unit 24 of the operating unit B1 in order to enter an operation command, the controller 29 judges that Surgical Case 2 has started, and increments the usage count of the working unit A1.

According to the above process of counting the usage count of the working unit 16 using the first preset time and the second preset time, the controller 29 determines whether or not the surgical case has been switched to another surgical case based on whether the operating unit 14 remains disconnected from the controller 29 within the second preset time. For example, the shortest period that is expected to be required for disconnecting the operating unit 14 from the controller 29 and for sterilizing the operating unit 14 is preset as the second preset time. If the operating unit 14 is disconnected from the controller 29 for sterilization and thereafter the operating unit 14 is reconnected to the controller 29, then since the second present time has elapsed, the controller 29 judges that the surgical case has been switched, and increments the usage count of the working unit 16 accordingly. Alternatively, if the operating unit 14 is replaced with another operating unit 14 due to an error, then the operating unit is highly likely to be replaced within the second preset time. When replacement of the operating unit 14 is completed within the second preset time, the usage count of the working unit 16 is prevented from being unduly incremented.

The usage count rule using the third preset time will be described below. The third preset time is applied while the first preset time also is being applied.

When the surgical case switches to another surgical case, it is possible to turn off the controller 29, or to disconnect the power cable 31 (see FIG. 1) and move the controller 29. If the power switch of the controller 29 is inadvertently turned off, or if the power cable 31 is inadvertently disconnected, then it is highly likely that the system of the controller 29 will be restored within a relatively short period of time, e.g., 10 minutes or shorter. Accordingly, it is determined whether the surgical case has been switched to another surgical case based on the fact that the controller 29 is turned off or the power cable 31 is disconnected for a period of time longer than the third preset time, e.g., 10 minutes. The third preset time is shorter than the first preset time, and may be equal to the second preset time.

When the controller 29 is restarted after power has not been supplied to the controller 29, or after the controller 29 has been turned off, i.e., after the controller 29 has been placed in a power-off state, if restarting of the controller 29 is completed within the third preset time from start of the power-off state, then the controller 29 judges that the surgical case has not been switched to another surgical case. Alternatively, if restarting of the controller 29 is completed beyond the third preset time from start of the power-off state, then the controller 29 judges that the surgical case has been switched to another surgical case, or that the surgical case has finished.

A specific example of a process of incrementing the usage count of the working unit 16, using the first preset time and the third preset time, will be described below with reference to FIG. 10. It is assumed that the first preset time is five hours, the third preset time is 10 minutes, and the limit usage count for the working unit 16 is 20. The symbols and graphic patterns used in FIG. 10 have the same meanings as those used in FIG. 7.

Figure 10:
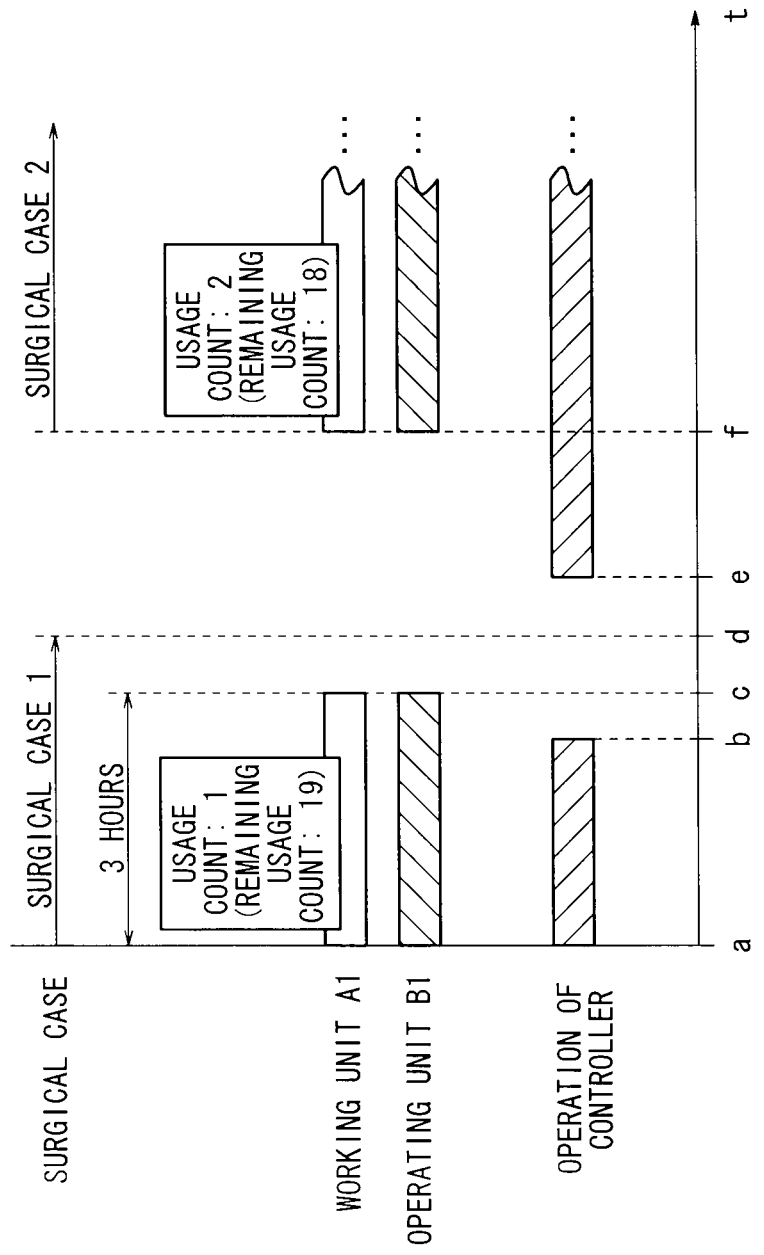
FIG. 10 is a diagram illustrative of switching between surgical cases based on a third preset time.

As shown in FIG. 10, at time "a", the operating unit B1 is connected to the controller 29, and the working unit A1 is installed on the operating unit B1. At the same time, the controller 29 recognizes individual identifying information of the working unit A1. When the operator operates the composite input unit 24 of the operating unit B1 in order to enter an operation command, the controller 29 judges that Surgical Case 1 has started, and increments the usage count of the working unit A1.

At time "b", the controller 29 is intentionally turned off to result in a power-off state, and counting down of the third preset time is started. Subsequently, at time "c", the working unit A1 and the operating unit B1 are disconnected from the controller 29. At time "d", which is 10 minutes later than time "b", since the controller 29 is still in a power-off state, the controller 29 judges that Surgical Case 1 has finished, according to a rule based on the third preset time.

If the controller 29 is turned off for some reason and is subsequently turned on immediately thereafter, so that activation of the system of the controller 29 is completed within 10 minutes from time "b", then counting down of the third preset time is stopped. In this case, the controller 29 judges that Surgical Case 1 has not yet finished.

At time "e", activation of the system of the controller 29 is completed and the controller 29 becomes fully operational. Subsequently, at time "f", the operating unit B1 is connected to the controller 29, and the working unit A1 is installed on the operating unit B1. At the same time, the controller 29 recognizes individual identifying information of the working unit A1. When the operator operates the composite input unit 24 of the operating unit B1 in order to enter an operation command, the controller 29 judges that Surgical Case 2 has started, and increments the usage count of the working unit A1.

Even when the controller 29 is inadvertently brought into a power-off state, the controller 29 is immediately turned on again and reactivated within the third preset time, so that the present surgical case is judged as being the same as the surgical case as that being performed when the controller 29 was turned off. As a result, the usage count of the working unit 16 is prevented from being unduly incremented. On the other hand, when the surgical case switches to another surgical case, typically, the third preset time has elapsed. Therefore, when the controller 29 is turned off while the surgical case is switching to another surgical case, since the third preset time has elapsed, the surgical case at the time the controller 29 was turned off is judged as being finished. Then, when the operating unit 14 is reconnected to the controller 29 at the next time, and the working unit 16 is installed on the operating unit 14, a subsequent surgical case is judged as starting, and the usage count of the working unit 16 is incremented accordingly.

When a surgical case is finished, the working unit 16 is cleaned and sterilized while the controller 29 remains in an energized state, and thereafter, the same working unit 16 is reconnected to the same controller 29 to perform a next surgical case. If the first preset time has not elapsed from start of the preceding surgical case, the operating unit 14 may remain disconnected from the controller 29 within the second preset time, depending on the time required for installation of the operating unit 14 on the controller 29. In this case, only under the surgical case ending condition, based on the second preset time and the third preset time, switching between the surgical cases may not be recognized, although in fact the present surgical case has been switched to the next surgical case. In such a case, the usage count of the working unit 16 may not be incremented appropriately.

According to the present embodiment, the controller 29, which has a plurality of N connection ports 27, may judge that the present surgical case has switched to a next surgical case, if the number of operating units 14 connected in the present surgical case reaches N+α, where a can be set to a suitable value, in view of the reliability of the manipulator system 10 and the ease with which the operator uses the manipulator system 10.

For example, if the reliability of the manipulator system 10 is high and the possibility that the operating unit 14 will suffer from an error is extremely low, then α may be set to "1". In this case, if an nth operating unit 14, where "n" is 1 greater than the number N of connection ports 27 during a surgical case, is connected to the controller 29 (e.g., if there are two connection ports, the third operating unit 14), then the controller 29 judges that the surgical case has been switched to another surgical case.

If the ease with which the operator uses the manipulator system 10 is given priority, in view of the possibility that the operating unit 14 may suffer from certain errors, then a may be set to "2". In this case, if the operating unit 14 suffers from a certain error and has to be replaced with another operating unit 14, then the controller 29 does not judge that the surgical case has been switched to another surgical case, because only one operating unit 14 has been replaced. However, if an nth operating unit 14, where "n" is 2 greater than the number N of connection ports 27 during a surgical case, is connected to the controller 29, then the controller 29 judges that the surgical case has been switched to another surgical case.

A specific example of a process of incrementing the usage count of the working unit 16 in the manipulator system 10, which includes the controller 29 with two connection ports 27, will be described below with reference to FIG. 11. It is assumed that α is set to "2", the first preset time is five hours, the second preset time is 10 minutes, the third preset time is 10 minutes, and the limit usage count for the working unit 16 is 20.

Figure 11:
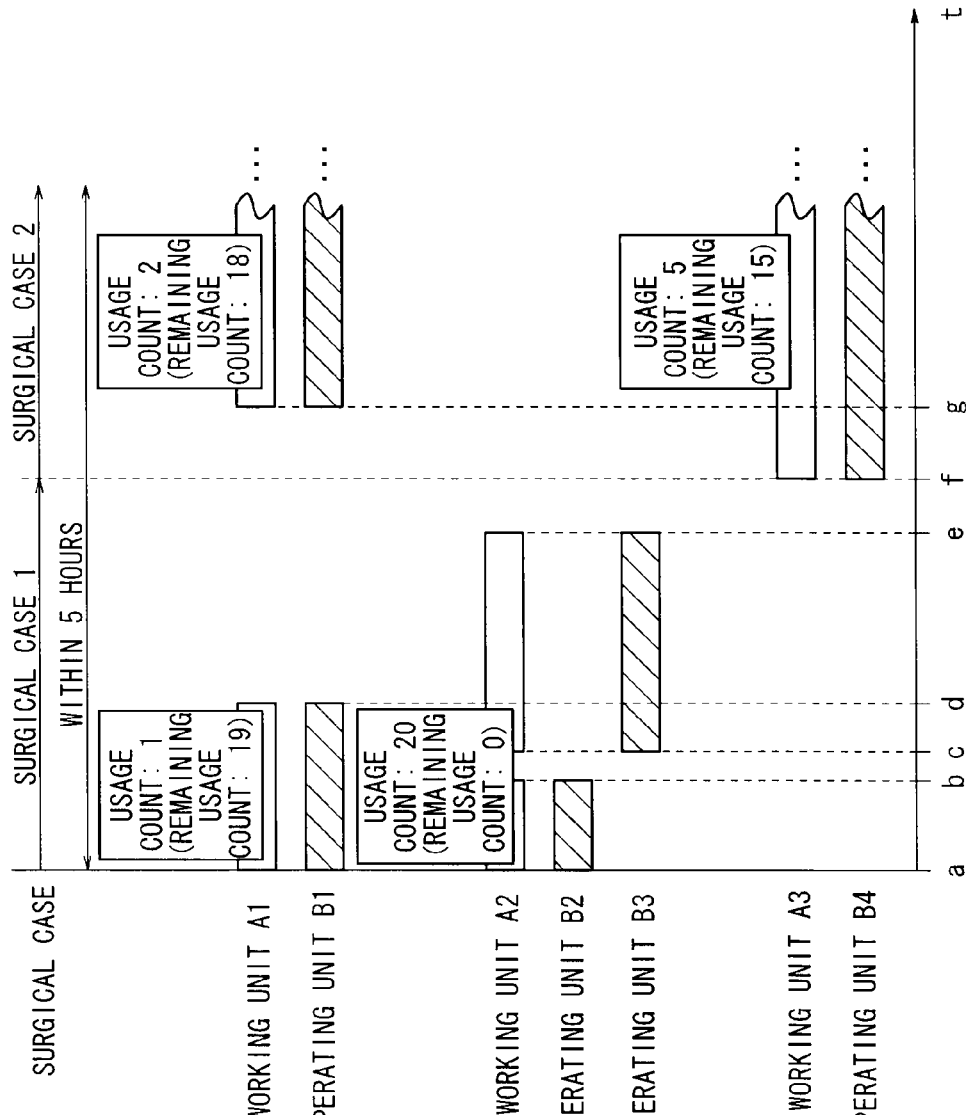
FIG. 11 is a diagram illustrative of switching between surgical cases while a fourth operating unit is connected to a controller.

As shown in FIG. 11, at time "a", the operating unit B1 is connected to the controller 29, and the working unit A1 is installed on the operating unit B1. At the same time, the controller 29 recognizes individual identifying information of the working unit A1. When the operator operates the composite input unit 24 of the operating unit B1 in order to enter an operation command, the controller 29 judges that Surgical Case 1 has started, and increments the usage count of the working unit A1. At time "a", the controller 29 also increments the usage count of the working unit A2 mounted on the operating unit B2.

At time "b", the operating unit B2 suffers from an error and is disconnected from the controller 29. At time "c", the working unit A2 is installed on another operating unit B3. Although the operating unit B3 is a third operating unit during Surgical Case 1, since N+α=4 is not yet reached, the controller 29 does not judge that Surgical Case 1 has been switched to Surgical Case 2.

At time "d", the operating unit B1 is disconnected from the controller 29 while the working unit A1 is sterilized and cleaned for use in a subsequent surgical case. At time "e", the operating unit B3 is disconnected from the controller 29. Thereafter, at time "f", within 10 minutes (the second preset time) from time "e", another operating unit B4 is connected to the controller 29, and a working unit A3 is installed on the operating unit B4. Since the operating unit B4 is a fourth operating unit during Surgical Case 1 and N+α=4 is reached, the controller 29 judges that Surgical Case 1 has finished and that Surgical Case 2 is started.

Accordingly, when an nth operating unit 14, where "n" is α greater than the number N of connection ports 27, is connected immediately to the controller 29 while the controller 29 remains energized, the controller 29 is prevented from failing to recognize that the surgical case actually has been switched to the next surgical case.

If α is set to "2", then when an nth operating unit 14, where "n" is 1 greater than the number N of connection ports 27, is connected to the controller 29, the controller 29 does not recognize that the surgical case has been switched to the next surgical case. Consequently, even if the operating unit has to be replaced with another operating unit due to an error, the usage count of the working unit 16, which has already been connected, is not unduly incremented. Therefore, the usage count of the working unit 16 can be incremented appropriately.

The controller 29 may judge the start and end of a surgical case based on the manner in which the working unit 16 is mounted and dismounted as well as the times at which the working unit 16 is mounted and dismounted, and can increment the usage count of the working unit 16 according to a modified usage count rule, which shall be described below. According to the modified usage count rule, the controller 29 has a function to define a surgical case based on at least one rule, and to increment the usage count of the working unit 16.

More specifically, the controller 29 increments the usage count of the working unit 16 for each surgical case, and cancels operation commands from the composite input unit 24 if the usage count of the working unit 16 exceeds the limit usage count (preset count). In other words, if the usage count of the working unit 16 exceeds the limit usage count, the controller 29 does not energize the motors 50a, 50b even though the composite input unit 24 may be operated.

According to the present embodiment, the controller 29 defines a surgical case according to first, second, and third rules, to be described below, and increments the usage count of the working unit 16 accordingly.

The first rule will first be described below. The first rule is a basic rule for defining a surgical case. When the working unit 16 is used in a surgical case, wherein the actual surgical operation continues for an extended period of time, if usage of the working unit 16 is regarded as a single usage event, then the working unit 16 may possibly suffer from a durability problem. According to the first rule, a maximum time of a surgical case is considered to be the first preset time (e.g., five hours), and the usage count of the working unit 16 is incremented based on the first preset time.

More specifically, according to the first rule, when the working unit 16 is installed on the operating unit 14, and the controller 29 recognizes individual identifying information of the working unit 16 while no rule is being applied, the controller 29 increments the usage count of the working unit 16. If the working unit 16 is installed beyond the first preset time, then the surgical case is switched to another surgical case each time that the first present time is exceeded, and the usage count of the working unit 16 is incremented for each of such surgical cases.

A specific example of a process of incrementing the usage count of the working unit 16 according to the first rule will be described below with reference to FIG. 12. It is assumed that the first preset time is five hours, and the limit usage count (preset count) for the working unit 16 is 20.

Figure 12:
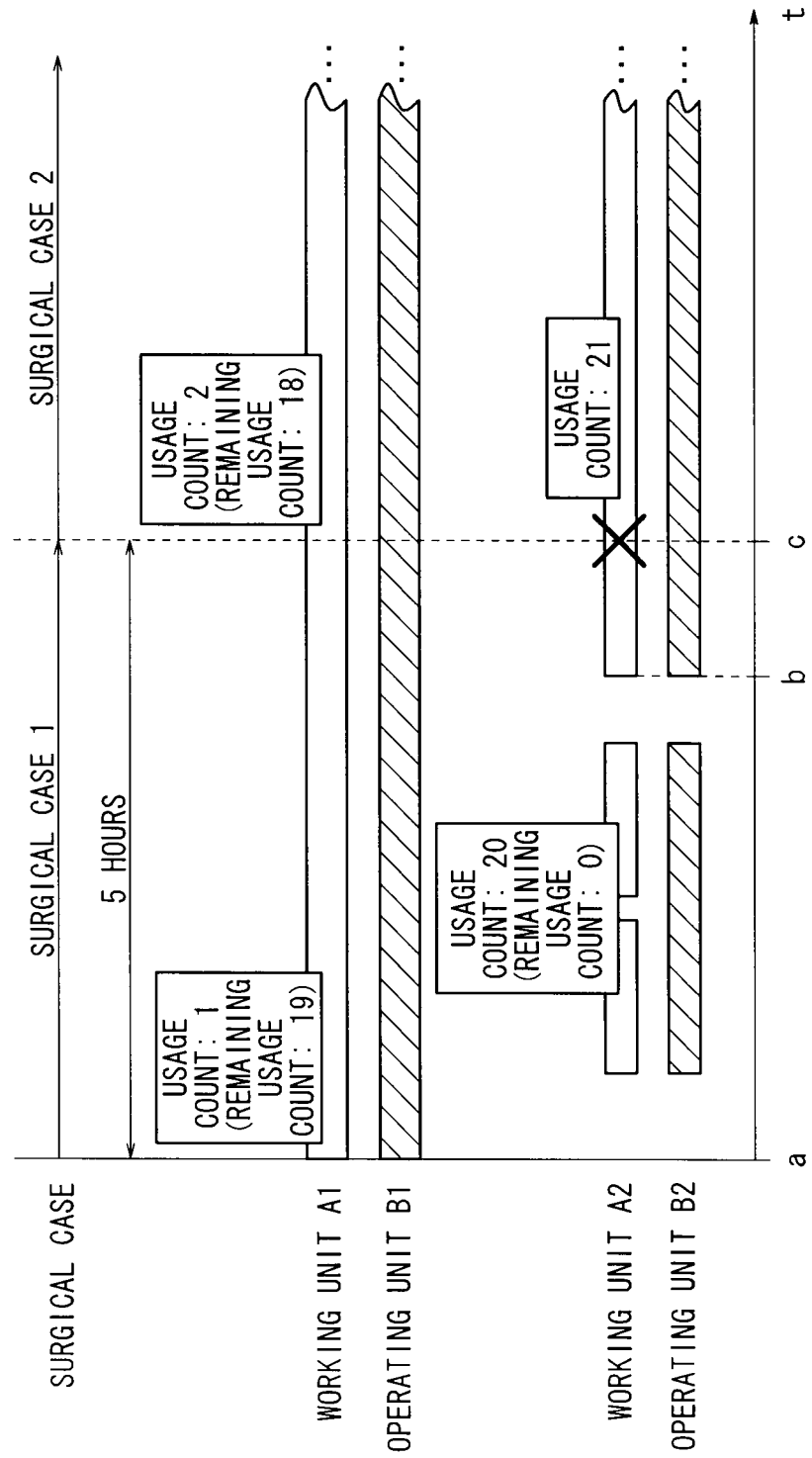
FIG. 12 is a diagram illustrative of a first rule for defining a surgical case.

As shown in FIG. 12, at time "a", the operating unit B1 is connected to the controller 29, and the working unit A1 is installed on the operating unit B1. At the same time, the controller 29 recognizes individual identifying information of the working unit A1. The controller 29 judges that Surgical Case 1 has started, increments the usage count of the working unit A1, and starts to count down the first rule using a timer function. At this time, it is assumed that the usage count of the working unit A1 is 1, i.e., the remaining usage count of the working unit A1 is 19.

When the operating unit B2 is connected to the controller 29 and the working unit A2 is installed on the operating unit B2 after time "a", the controller 29 recognizes individual identifying information of the working unit A2 and increments the usage count of the working unit A2. At this time, it is assumed that the usage count of the working unit A2 is 20, i.e., the remaining usage count of the working unit A2 is 0.

If the operating unit B2 and the working unit A2 are disconnected slightly before time "b", and thereafter are reconnected at time "b", then since the usage count of the working unit A2 would be incremented during the same surgical case, the usage count of the working unit A2 is not incremented.

At time "c", since the first rule has been used for five hours (the first preset time), the controller 29 judges that the second surgical case (next surgical case) has started, and increments the usage counts of the working units A1, A2. The working unit A2 is disabled because the usage count thereof has exceeded the limit usage count thereof. In other words, even if the composite input unit 24 is operated at or after time "c", the controller 29 cancels any operation commands from the composite input unit 24, and does not energize the motors 50a, 50b.

Since the controller 29 determines whether or not the surgical case has been switched to the next surgical case based on the manner in which the working unit 16 is mounted and dismounted, and times at which the working unit 16 is mounted and dismounted, the controller 29 can appropriately define a surgical case by setting a condition with respect to the manner in which the working unit 16 is mounted and dismounted, as well as the times at which the working unit 16 is mounted and dismounted. As a result, the controller 29 can appropriately increment the usage count of the working unit 16. In other words, the controller 29 sets the first preset time so as to correspond to a maximum time which is expected to be required for one surgical case (surgical operation). Thus, the controller 29 regards usage of the working unit 16 within the first preset time as a single usage event, and increments the usage count of the working unit 16 accordingly.

The controller 29 judges that the surgical case has been switched to the next surgical case each time that the usage time of the working unit 16 exceeds the first preset time. Therefore, if the surgical case requires a considerable length of time, then the controller 29 regards usage of the working unit 16 as a plurality of usage events, and increments the usage count of the working unit 16 accordingly.

If the usage count of the working unit 16 is in excess of the limit usage count (preset count) of the working unit 16, then the controller 29 cancels any operation commands that are entered from the composite input unit 24. Therefore, even when the operator operates the composite input unit 24, the motors 50a, 50b are not energized and the distal-end working unit 12 including the end effector 19 is not actuated. Consequently, the working unit 16, the usage count of which has reached the limit usage count, is forcibly disabled.

The second rule will be described below. The second rule is applied while the first rule also is being applied. Thus, the second rule is subordinate to the first rule.

According to the second rule, it is assumed that while the controller 29 remains energized, the operating unit 14 is disconnected from the controller 29, and thereafter the same operating unit 14 or another operating unit 14 is reconnected to the controller 29. If the operating unit 14 is reconnected to the controller 29 within the second preset time after the operating unit 14 has been disconnected from the controller 29, then the controller 29 judges that the surgical case has not been switched to another surgical case. At this time, the controller 29 does not increment the usage count of the connected working unit 16. If the operating unit 14 is connected to the controller 29 beyond the second preset time after the operating unit 14 has been disconnected from the controller 29, then the controller 29 judges that the surgical case has been switched to another surgical case, and increments the usage count of the connected working unit 16. According to the second rule, the count rule described above with referenced to FIG. 9 is applied to the modified usage count rule.

A specific example of a process of incrementing the usage count of the working unit 16 according to the second rule will be described below with reference to FIG. 13. It is assumed that the first preset time is five hours, the second preset time is 10 minutes, and the limit usage count for the working unit 16 is 20.

As shown in FIG. 13, at time "a", the operating unit B1 is connected to the controller 29, and the working unit A1 is installed on the operating unit B1. At the same time, the controller 29 recognizes individual identifying information of the working unit A1. The controller 29 judges that Surgical Case 1 has started, increments the usage count of the working unit A1, and starts to count down the first rule. At this time, it is assumed that the usage count of the working unit A1 is 1, i.e., the remaining usage count of the working unit A1 is 19.

At time "b", the working unit A1 and the operating unit B1 are disconnected from the controller 29, and counting down of the second rule begins. At this time, an operating unit 14 is not connected to the controller 29. At time "c", which is 9 minutes after time "b", the operating unit B2 is connected to the controller 29, and the controller 29 stops counting down the second rule. The first rule is continuously counted down between time "b" and time "c".

At time "d", the working unit A2 is installed on the operating unit B2, and the controller 29 increments the usage count of the working unit A2. At time "e", the operating unit B2 is disconnected from the controller 29, and the controller 29 starts to count down the second rule. At time "f", after elapse of 10 minutes from time "e", the controller 29 judges that Surgical Case 1 has ended.

At time "g", the operating unit B2 is connected to the controller 29, and the working unit A2 is installed on the operating unit B2. Since the usage count of the working unit A2 has reached the upper limit thereof, the working unit A2 cannot be used. At this time, the controller 29 judges that a new surgical case has not been started, and does not count down the first rule.

At time "h", the operating unit B1 is connected to the controller 29, and the working unit A1 is installed on the operating unit B1. The controller 29 judges that Surgical Case 2 has started, and increments the usage count of the working unit A1.

According to the second rule, as described above, the controller 29 determines whether the surgical case has been switched to another surgical case, based on whether or not the operating unit 14 has been disconnected from the controller 29 continuously within the second preset time. By setting a shortest time, which is expected to be required to remove the operating unit 14 from the controller 29 for sterilization, as the second preset time, for example, the controller 29 is capable of determining whether or not the surgical case has been switched to another surgical case, or whether the operating unit 14 has been replaced due to an error. As a result, the controller 29 is capable of incrementing the usage count of the working unit 16 appropriately.

The third rule will be described below. The third rule is applied while the first rule also is being applied. The third rule thus is subordinate to the first rule.

According to the third rule, it is assumed that the controller 29 is turned off to result in a power-off state, and thereafter is restarted. If restarting of the controller 29 is completed within the third preset time from start of the power-off state, then the controller 29 judges that the surgical case has not been switched to another surgical case. If restarting of the controller 29 is completed beyond the third preset time from start of the power-off state, then the controller 29 judges that the surgical case has been switched to another surgical case. According to the third rule, the count rule described above with referenced to FIG. 10 is applied to the modified usage count rule.

A specific example of a process for incrementing the usage count of the working unit 16 according to the third rule will be described below with reference to FIG. 14. It is assumed that the first preset time is five hours, the third preset time is 1 minute, and the limit usage count for the working unit 16 is 20. According to the third rule, it is assumed that when supply of electric power from an external power supply to the controller 29 is cut off, the controller system is automatically turned off. After having been turned off, the controller 29 requires about 30 seconds to restart the controller system.

As shown in FIG. 14, at time "a", the operating unit B1 is connected to the controller 29, and the working unit A1 is installed on the operating unit B1. At the same time, the controller 29 recognizes individual identifying information of the working unit A1. The controller 29 judges that Surgical Case 1 has started, increments the usage count of the working unit A1, and starts to count down the first rule. At this time, it is assumed that the usage count of the working unit A1 is 1, i.e., the remaining usage count of the working unit A1 is 19.

At time "b", the power cable 31 is disconnected from the controller 29, which is turned off. At time "c", which is 20 seconds from time "b", the power cable 31 is connected to the controller 29. At time "d", which is 55 seconds from time "b", starting of the system of the controller 29 is completed, and the controller 29 stops counting down the third rule.

The first rule is continuously counted down between time "b" and time "d". At time "e", the power cable 31 is disconnected from the controller 29, which is turned off. At time "f", which is 35 seconds from time "e", the power cable 31 is connected to the controller 29, thereby turning on the controller 29. At time "g", which is 65 seconds from time "e", starting of the system of the controller 29 is completed. Since 65 seconds have elapsed from time "e", the controller 29 judges that Surgical Case 1 has been completed.

At time "h", the operating unit B1 is connected to the controller 29, and the working unit A1 is installed on the operating unit B1. The controller 29 judges that Surgical Case 2 has started and increments the usage count of the working unit A1.

According to the third rule described above, the controller 29 determines whether the surgical case has been switched to another surgical case based on whether the controller 29 has been restarted within the third preset time from start of the power-off state. Therefore, if the power switch of the controller 29 is inadvertently turned off, or if the power cable 31 is inadvertently disconnected, then the controller 29 can determine whether the surgical case has been switched to another surgical case or whether the controller 29 has been inadvertently turned off, by setting the third preset time so as to correspond to a maximum time, which is expected to be required to restart the controller 29. As a result, the controller can increment the usage count of the working unit 16 appropriately.

According to the modified usage count rule, the time at which the controller 29 recognizes individual identifying information of the working unit 16 is used as a reference time for determining start of a surgical case (determining condition). However, the time when the composite input unit 24 is operated in order to enter an operation command, while the working unit 16 is being mounted on the operating unit 14 and while the operating unit 14 is being connected to the controller 29, may also be used as a reference time for determining start of a surgical case.

In the above embodiment, the usage count of the working unit 16 is incremented when a surgical case has started, i.e., when the controller 29 recognizes the individual identifying information of the working unit 16. Alternatively, the usage count of the working unit 16 may be incremented upon completion of a surgical case.

Although certain preferred embodiments of the present invention have been shown and described in detail, it should be understood that various changes and modifications may be made to such embodiments without departing from the scope of the invention as set forth in the appended claims.

What is claimed is:

1. A medical manipulator system comprising:
   a manipulator including
      a working unit with an end effector mounted on a distal end thereof,
      an operating unit having an operation input unit operable to enter an operation command, and
      an actuator energizable depending on the operation command entered by the operation input unit for actuating the end effector, the working unit being detachably mounted on the operating unit;
   a controller for controlling the actuator and incrementing a usage count of the working unit, the operating unit being connectable to the controller; and
   a usage history holder for holding usage history data of the working unit,
   wherein the working unit includes an ID holder for holding individual identifying information of the working unit,
   wherein the operating unit includes an ID detector for detecting the individual identifying information held by the ID holder,
   wherein the controller judges starting and ending of a surgical case based on a manner in which the working unit is mounted and dismounted and the times at which the working unit is mounted and dismounted, counts a single usage event of the working unit when the surgical case has started or ended, and disables the working unit if the usage count of the working unit exceeds a preset count,
   wherein the controller increments the usage count of the working unit each time a surgical case has started and when the working unit satisfies a usage starting condition, and increments the usage count of the working unit each time a first preset time is exceeded if the working unit is used beyond the first preset time from a time when the controller recognizes that the working unit starts to be used, during a surgical case, and
   wherein if the usage count of the working unit exceeds the preset count because the working unit has been used beyond the first preset time during the surgical case, the controller allows the working unit to operate until a special preset time is reached, at which time the working unit is disabled by the controller, the special preset time is longer than the first preset time and corresponding to an expected length of the surgical case.

2. The medical manipulator system according to claim 1, wherein the controller measures a parameter that increases as the working unit is used, and increments the usage count of the working unit when the parameter reaches a reference value, which is determined depending on the usage count of the working unit during a surgical case even before the first preset time has elapsed.

3. The medical manipulator system according to claim 1, wherein if the operating unit is disconnected from the controller and thereafter is reconnected to the controller while the controller remains energized, the controller:
- judges that the surgical case has not been switched to another surgical case when the operating unit is reconnected to the controller within a second preset time, which is shorter than the first preset time, after the operating unit has been disconnected from the controller; and
- judges that the surgical case has been switched to another surgical case when the operating unit is reconnected to the controller beyond the second preset time after the operating unit has been disconnected from the controller.

4. The medical manipulator system according to claim 3, wherein the controller has N connection ports for detachable connection to operating units, and the controller judges that the surgical case has been switched to another surgical case when the number of operating units connected to the controller during the surgical case reaches N+α, where α relates to the reliability of the manipulator system.

5. The medical manipulator system according to claim 4, wherein the α is 2.

6. The medical manipulator system according to claim 4, wherein α is 1, indicating that the possibility of the operating unit suffering from an error is low.

7. The medical manipulator system according to claim 1, wherein if the controller is restarted after the controller has not been supplied with electric power, or has been turned off to result in a power-off state, the controller:
- judges that the surgical case has not been switched to another surgical case when restarting of the controller is completed within a third preset time, which is shorter than the first preset time, after start of the power-off state; and
- judges that the surgical case has been switched to another surgical case when restarting of the controller is completed beyond the third preset time after start of the poweroff state.

8. The medical manipulator system according to claim 1, wherein in a parallel use of a plurality of working units, whether the first preset time is exceeded or not is judged per working unit.

9. The medical manipulator system according to claim 1, wherein the usage history data is stored on the controller.

10. A medical manipulator system comprising:
- a manipulator including
  - a working unit with an end effector mounted on a distal end thereof,
  - an operating unit having an operation input unit operable to enter an operation command, and
  - an actuator energizable depending on the operation command entered by the operation input unit for actuating the end effector, the working unit being detachably mounted on the operating unit;
- a controller for controlling the actuator and incrementing a usage count of the working unit, the operating unit being connectable to the controller; and
- a usage history holder for holding usage history data of the working unit,
- wherein the working unit includes an ID holder for holding individual identifying information of the working unit,
- wherein the operating unit includes an ID detector for detecting the individual identifying information held by the ID holder,
- wherein the controller judges starting and ending of a surgical case based on a manner in which the working unit is mounted and dismounted and the times at which the working unit is mounted and dismounted, counts a single usage event of the working unit when the surgical case has started or ended, and disables the working unit if the usage count of the working unit exceeds a preset count,
- wherein the controller defines a surgical case based on at least one rule, determines whether the surgical case has been switched to another surgical case, sets a first preset time for a surgical case, and increments the usage count of the working unit for each surgical case, the at least one rule including a rule that the controller judges that the surgical case has been switched to another surgical case when the first preset time is exceeded from a time when the controller recognizes that the surgical case begins, and
- wherein if the usage count of the working unit exceeds the preset count because the working unit has been used beyond the first preset time during the surgical case, the controller allows the working unit to operate until a special preset time is reached, at which time the working unit is disabled by the controller, the special preset time is longer than the first preset time and corresponding to an expected length of the surgical case.

11. The medical manipulator system according to claim 10, wherein if the operating unit is disconnected from the controller and thereafter is reconnected to the controller while the controller remains energized, the controller:
- judges that the surgical case has not been switched to another surgical case when the operating unit is reconnected to the controller within a second preset time, which is shorter than the first preset time, after the operating unit has been disconnected from the controller; and
- judges that the surgical case has been switched to another surgical case when the operating unit is reconnected to the controller beyond the second preset time after the operating unit has been disconnected from the controller.

12. The medical manipulator system according to claim 11, wherein the controller has N connection ports for detachable connection to operating units, and the controller judges that the surgical case has been switched to another surgical case when the number of operating units connected to the controller during the surgical case reaches N+α, where α relates to the reliability of the manipulator system.

13. The medical manipulator system according to claim 12, wherein the α is 2.

14. The medical manipulator system according to claim 12, wherein α is 1, indicating that the possibility of the operating unit suffering from an error is low.

15. The medical manipulator system according to claim 10, wherein if the controller is restarted after the controller has not been supplied with electric power, or has been turned off to result in a power-off state, the controller:
- judges that the surgical case has not been switched to another surgical case when restarting of the controller is completed within a third preset time, which is shorter than the first preset time, after start of the power-off state; and judges that the surgical case has been switched to another surgical case when restarting of the controller is completed beyond the third preset time after start of the poweroff state.

16. The medical manipulator system according to claim 10, wherein in a parallel use of a plurality of working units, whether the first preset time is exceeded or not is judged per working unit.

17. The medical manipulator system according to claim 10, wherein the usage history data is stored on the controller.

18. A medical manipulator system, comprising:
a manipulator including
a working unit with an end effector mounted on a distal end thereof,
an operating unit having an operation input unit operable to enter an operation command, and
an actuator energizable depending on the operation command entered by the operation input unit for actuating the end effector, the working unit being detachably mounted on the operating unit;
a controller for controlling the actuator and incrementing a usage count of the working unit, the operating unit being connectable to the controller; and
a usage history holder for holding usage history data of the working unit,
wherein the controller judges starting and ending of a surgical case based on a manner in which the working unit is mounted and dismounted and the times at which the working unit is mounted and dismounted, counts a single usage event of the working unit when the surgical case has started or ended, and disables the working unit if the usage count of the working unit exceeds a preset count,
wherein the controller increments the usage count of the working unit each time a surgical case has started and when the working unit satisfies a usage starting condition, and increments the usage count of the working unit each time a first preset time is exceeded if the working unit is used beyond the first preset time from a time when the controller recognizes that the working unit starts to be used, during surgical case, and
wherein the controller has N connection ports for detachable connection to operating units, and the controller judges that the surgical case has been switched to another surgical case when the number of operating units connected to the controller during the surgical case reaches N+α, where α relates to the reliability of the manipulator system.

* * * * *